(12) United States Patent
Figueroa Perez et al.

(10) Patent No.: US 8,399,471 B2
(45) Date of Patent: Mar. 19, 2013

(54) ARYL-OR HETEROARYL-SUBSTITUTED PYRIDO[2,3-D] PYRIMIDINES AND PHARMACEUTICAL COMPOSITIONS OF THE SAME

(75) Inventors: Santiago Figueroa Perez, Leverkusen (DE); Peter Kolkhof, Wuppertal (DE); Lars Bärfacker, Oberhausen (DE); Ingo Flamme, Reichshof (DE); Karl-Heinz Schlemmer, Wuppertal (DE); Alexander Kuhl, Hagen (DE); Rolf Grosser, Leverkusen (DE); Klaus Münter, Mülfrath (DE); Andreas Knorr, Erkrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 711 days.

(21) Appl. No.: 12/303,369

(22) PCT Filed: May 25, 2007

(86) PCT No.: PCT/EP2007/004690
§ 371 (c)(1),
(2), (4) Date: Aug. 7, 2009

(87) PCT Pub. No.: WO2007/140894
PCT Pub. Date: Dec. 13, 2007

(65) Prior Publication Data
US 2010/0035902 A1 Feb. 11, 2010

(30) Foreign Application Priority Data
Jun. 7, 2006 (DE) .......................... 10 2006 026 583

(51) Int. Cl.
*C07D 471/04* (2006.01)
*A61K 32/519* (2006.01)
*A61P 9/00* (2006.01)
(52) U.S. Cl. ................. 514/264.1; 514/264.11; 544/279
(58) Field of Classification Search .................. 544/279; 514/264.1, 264.22, 264.11
See application file for complete search history.

(56) References Cited

U.S. PATENT DOCUMENTS

| | | | |
|---|---|---|---|
| 4,621,082 A * | 11/1986 | Meyer et al. ............. | 514/211.15 |
| 4,681,882 A | 7/1987 | Kleinschroth et al. | |
| 4,698,341 A | 10/1987 | Satzinger et al. | |
| 4,711,901 A | 12/1987 | Satzinger et al. | |
| 4,751,228 A | 6/1988 | Kleinschroth et al. | |
| 4,760,081 A | 7/1988 | Satzinger et al. | |
| 4,762,837 A | 8/1988 | Kleinschroth et al. | |
| 2010/0305052 A1 | 12/2010 | Figueroa Perez et al. | |
| 2011/0245209 A1 * | 10/2011 | Xiao et al. ................ | 514/161 |

FOREIGN PATENT DOCUMENTS

| EP | 0133530 A2 | 2/1985 |
|---|---|---|
| EP | 0173933 A1 | 3/1986 |
| EP | 0180834 | 5/1986 |
| EP | 0189898 A1 | 8/1986 |
| EP | 0234516 A1 | 9/1987 |
| WO | WO-02/10164 A2 | 2/2002 |
| WO | WO 2005/087740 | 9/2005 |
| WO | WO-2005/097118 A1 | 10/2005 |
| WO | WO-2006/066011 A2 | 6/2006 |
| WO | WO-2007/009670 A1 | 1/2007 |

OTHER PUBLICATIONS

Takeda, et al., Hypertens. Res., vol. 27, #11 (2004), 781-789.*
Pitt, et al., Europ. J. Heart Failure, vol. 13, #7, 755-764 (Feb. 4, 2011).*
Hayashi, et al., Circulation. May 27, 2003;107(20):2559-65.*
Schmidt, et al., Europ. Heart J., (2010), 31, 1655-1662.*
R. E. Booth et al.: "Aldosterone," Advances in Physiology Rducation, vol. 26, No. 1, Mar. 2002, pp. 8-20.
B. Pitt et al.: "Eplerenone, A Selective Aldosterone Blocker, in Patients with Left Ventricular Dysfunction after Myocardial Infarction," The New England Journal of Medicine, vol. 348, No. 14, Apr. 3, 2003, pp. 1309-1321.
L. Seiler et al.: "Der Aldosteron-Renin-Quotient bei Sekundarer Hypertonie," Herz, vol. 28, No. 8, 2003, 686-691.
H. A. Kuhn et al.: Innere Medizin—Ein Lehrbuch fur Studierende der Medizin und Arzte Begrundet von Ludwig Heilmeyer, Springer-Verlag, Berlin, Heidelberg, New York, 1982.
M. A. Zaman et al.; "Drugs Targeting the Renin-Angiotension-Aldosterone System," Nature Reviews Drug Discovery, vol. 1, Aug. 2002, pp. 621-636.
Ehlert, et al.:"The Binding of [3H]Nitrendipine to Receptors for Calcium Channel Antagonists in the Heart, Cerebral Cortex, and Ileum of Rats," Life Sciences, 1982, 30(25):2191-2202.
Funder, "Mineralcorticoid Receptors and Cardiovascular Damage: It's Not Just Aldosterone," Hypertension, 2006, 47:634-635.
Gould, et al.:"[3H]Nitrendipine-labeled Calcium Channels Discriminate Inorganic Calcium Agonist and Antagonist," Proc. Natl. Acad. Sci., Jun. 1982, 79:3656-3660.
Hinschberger, et al.:"1,2,3,4,5,6-Hexahydrobenzo[h][1,6]naphthyridin-5-ones: 5-HT7 Receptor Affinity," Pharm. Pharmacol. Commun., 2000, 6:67-71.
Kleinschroth, et al.:"Synthese Neur 1,6-Naphthyridine durch Aminomethin-ylierung von 1,4-Dihydropyridinen," Synthesis, Oct. 1986, pp. 859-860.

(Continued)

Primary Examiner — Susanna Moore
Assistant Examiner — Cecilia M Jaisle
(74) Attorney, Agent, or Firm — Karen B. King

(57) ABSTRACT

The present application relates to novel aryl- or heteroaryl-substitued pyrido[2,3-d] pyrimidines of formula (I), pharmaceuitical compositions of the same, and a process for their preparation. Formula(I) is:

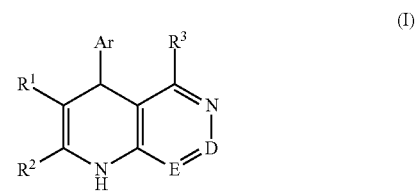

wherein Ar is an aryl or heteroaryl substituent, and $R^1$, $R^2$, $R^3$, Ar, D, and E are as defined in the specification. Compounds and compositions of the present invention can be used in the treatment and/or prophylaxis of various disorders in humans and animals, including aldosteronism, high blood pressure, chronic heart failure, the sequelae of a myocardial infarction, cirrhosis of the liver, renal failure, and stroke.

6 Claims, No Drawings

OTHER PUBLICATIONS

Manesiotis, et al.:"Improved Imide Receptors by Imprinting Using Pyrimidine-Based Fluorescent Reporter Monomers," J. Org. Chem., 2005, 70(7):2729-2738.

Nugent, et al.:"Pyrimidine Thioethers: A Novel Class of HIV-1 Reverse TranscriptaseInhibitors with Activity Against BHAP-Resistant HIV," J. Med. Chem., 1998, 41:3793-3803.

Pietzonka, et al.:"Alkylations of (R,R)-2-t-Butyl-6-methyl-1,3-dioxan-4-ones which are not Possible with Lithium Amides may be Achieved with a Schwesinger P4 Base," Chemische Berichte, Jan. 25, 2006, 124(8):1837-1843.

Pitt, et al.:"The Effect of Spironalactone on Morbidity and Mortality in Patients with Severe Heart Failure," The New England Journal of Medicine, Sep. 2, 1999, 341(10):709-717.

Rocha, et al.:"Rationale for the Use of Aldosterone Antagonists in Congestive Heart Failure," Drugs, 2002, 62(5):723-731.

Schwesinger, et al.:"Peralkylated Polyaminophosphazenes-Extremely Strong, Neutral Nitrogen Bases," Angewandte Chemie International Edition in English, Dec. 22, 2003, 26(11):1167-1169.

Taylor, et al.:"Pteridines. VII. The Synthesis of 2-Alkylaminopteridines1,2," J. Am. Chem. Soc., 1952, 74(7):1644-1647.

Weihong, "Sterioid Receptor Heterodimerization Demonstrated in vitro and in vivo," Proc Natl. Acad. Sci USA, Dec. 1995, 92:12480-12484.

Werner, et al:"Hydrophobic Properties of Novel Dihydronaphthyridine Calcium Antagonist and Biological Activity in Porcine Isolated Cardiac and Vascular Smooth Muscle," Naunyn-Schmiedeberg's Arch Pharmacol, 1991, 344:337-344.

West, Anthony R.:"Solid State Chemistry and its Applications," Wiley, New York, 1988, pp. 358 & 365.

Zannad, et al.:"Effect of MR Blockade on Collagen Formation and Cardiovascular Disease with a Specific Emphasis on Heart Failure," Heart Failure Reviews, 2005, 10:71-78.

U.S. Appl. No. 12/303,719, 371 filed Jun. 28, 2010.

U.S. Appl. No. 12/526,951, filed Jan. 12, 2010.

* cited by examiner

ARYL-OR HETEROARYL-SUBSTITUTED PYRIDO[2,3-D] PYRIMIDINES AND PHARMACEUTICAL COMPOSITIONS OF THE SAME

RELATED APPLICATIONS/PATENTS AND INCORPORATION BY REFERENCE

This application is a National Stage Application filed under 35 U.S.C. §371 based on International Application No. PCT/EP2007/004690, filed May 25, 2007, which claims priority to German Patent Application Number 102006026583.1, filed Jun. 7, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel aryl-substituted heterobicyclic compounds, a process for their preparation, their use for the treatment and/or prophylaxis of diseases, and their use for the manufacture of medicaments for the treatment and/or prophylaxis of diseases, especially cardiovascular disorders.

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R. E. Booth, J. P. Johnson, J. D. Stockand, *Adv. Physiol. Educ.* 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor, in the circulating blood and counteracts, via the renin-angiotensin-aldosterone system, critical losses of volume by on the one hand increasing the blood pressure (angiotensin II effect), and on the other hand, by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn this is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post acute myocardial infarction through the use of aldosterone antagonists [B. Pitt, F. Zannad, W. J. Remme et al., *N. Engl. J. Med.* 341, 709-717 (1999); B. Pitt, W. Remme, F. Zannad et al., *N. Engl. J. Med.* 348, 1309-1321 (2003)]. It was possible to achieve this inter alia by reducing the incidence of sudden cardiac death.

According to recent studies, a not inconsiderable number of patients suffering from essential hypertension are also found to have a so-called normokalemic variant of primary hyperaldosteronism [prevalence up to 11% of all hypertensives: L. Seiler and M. Reincke, *Der Aldosteron-Renin-Quotient bei sekundärer Hypertonie*, Herz 28, 686-691 (2003)]. The best diagnostic method for normokalemic hyperaldosteronism is the aldosterone/renin quotient of the corresponding plasma concentrations, so that relative elevations in aldosterone in relation to the renin plasma concentrations can also be diagnosed and eventually treated. For this reason, a hyperaldosteronism diagnosed in connection with essential hypertension is a starting point for a causal and prophylactically worthwhile therapy.

Far less common than the types of hyperaldosteronism detailed above are pathological states in which the impairment either is to be found in the hormone-producing cells of the adrenal itself, or the number or mass thereof is increased through hyperplasia or proliferation. Adenomas or diffuse hyperplasias of the adrenal cortex are the commonest cause of the primary hyperaldosteronism referred to as Conn's syndrome, the leading symptoms of which are hypertension and hypokalemic alkalosis. The priority here too, besides surgical removal of the diseased tissue, is medical therapy with aldosterone antagonists [H. A. Kühn and J. Schirmeister (Editors), *Innere Medizin*, 4th edition, Springer Verlag, Berlin, 1982].

Another pathological state associated typically with an elevation of the plasma aldosterone concentration is advanced cirrhosis of the liver. The cause of the aldosterone elevation in this case is mainly the restricted aldosterone breakdown resulting from the impairment of liver function. Volume overload, edema and hypokalemia are the typical consequences, which can be successfully alleviated in clinical practice by aldosterone antagonists.

The effects of aldosterone are mediated by the mineralocorticoid receptor which has an intracellular location in the target cells. The aldosterone antagonists available to date have, like aldosterone itself, a basic steroid structure. The utility of such steroidal antagonists is limited by their interactions with the receptors of other steroid hormones, which in some cases lead to considerable side effects such as gynecomastia and impotence and to discontinuation of the therapy [M. A. Zaman, S. Oparil, D. A. Calhoun, *Nature Rev. Drug Disc.* 1, 621-636 (2002)].

The use of potent, non-steroidal antagonists which are more selective for the mineralocorticoid receptor provides the possibility of avoiding this profile of side effects and thus achieving a distinct therapeutic advantage.

The object of the present invention is to provide novel compounds which can be used as selective mineralocorticoid receptor antagonists for the treatment of disorders, especially cardiovascular disorders.

EP 0 133 530-A, EP 0 173 933-A, EP 0 189 898-A and EP 0 234 516-A disclose 4-aryl-substituted 1,4-dihydro-1,6-naphthyridines and -naphthyridinones having a calcium-antagonistic effect for the treatment of vascular disorders. In addition, 1,4-dihydro-1,6-naphthyridine derivatives are claimed in WO 02/10164 as potassium channel openers for the treatment of various, in particular urological, disorders. 4-Fluorenonyl- and 4-chromenonyl-1,4-dihydropyridine derivatives are described as mineralocorticoid receptor antagonists in WO 2005/087740 and WO 2007/009670. WO 2006/066011 discloses 4-aryl-3-cyano-1,4-dihydropyridine-5-carboxylic esters and carboxamides as in some cases dual modulators of steroid hormone receptors and of the L-type calcium channel, and WO 2005/097118 claims compounds having a 4-aryl-1,4-dihydropyridine core structure as aldosterone receptor antagonists.

The present invention relates to compounds of the general formula (I)

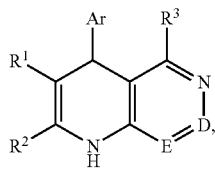

in which
D is N or C—$R^4$ in which
    $R^4$ is hydrogen, $(C_1\text{-}C_6)$-alkyl, trifluoromethyl, $(C_1\text{-}C_6)$-alkoxy, trifluoromethoxy, $(C_1\text{-}C_6)$-alkylthio, amino, mono-$(C_1\text{-}C_6)$-alkylamino or di-$(C_1\text{-}C_6)$-alkylamino,
E is N or C—$R^5$ in which
    $R^5$ is hydrogen or $(C_1\text{-}C_4)$-alkyl,
where either D is C—$R^4$ and E is N or D is N and E is C—$R^5$,
Ar is a group of the formula

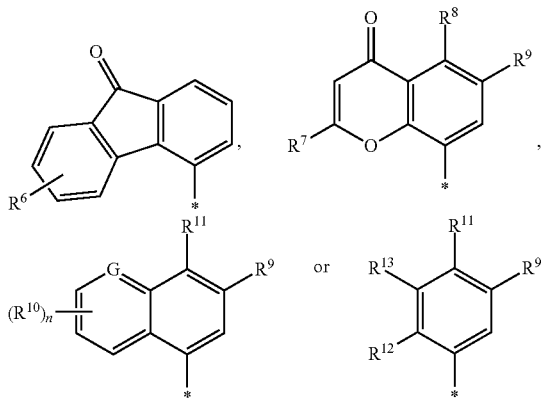

in which
* is the linkage point,
$R^6$ is hydrogen or halogen,
$R^7$ is methyl or ethyl, $R^8$ is hydrogen, fluorine, chlorine, cyano, nitro, trifluoromethyl or $(C_1\text{-}C_4)$-alkyl,
$R^9$ is hydrogen or fluorine,
$R^{10}$ is halogen, $(C_1\text{-}C_4)$-alkyl, trifluoromethyl, $(C_1\text{-}C_4)$-alkoxy or trifluoromethoxy,
$R^{11}$ is cyano or nitro,
$R^{12}$ is hydrogen, halogen, $(C_1\text{-}C_4)$-alkyl, $(C_1\text{-}C_4)$-alkoxy, $(C_1\text{-}C_4)$-alkylthio or di-$(C_1\text{-}C_4)$-alkylamino, it being possible for the alkyl group in said $(C_1\text{-}C_4)$-alkyl, $(C_1\text{-}C_4)$-alkoxy and $(C_1\text{-}C_4)$-alkylthio radicals in each case to be substituted up to three times by fluorine,
  or
  phenyl, which may be substituted by halogen, $(C_1\text{-}C_4)$-alkyl or trifluoromethyl,
$R^{13}$ is hydrogen, halogen or $(C_1\text{-}C_4)$-alkyl,
G is CH, C—$R^{10}$ or N,
and
n is the number 0, 1 or 2,
  it being possible in the case where the substituent $R^{10}$ occurs more than once for its meanings to be identical or different,
$R^1$ is cyano, nitro or a group of the formula —C(=O)—$R^{14}$ or —C(=O)—O—$R^{15}$ in which
  $R^{14}$ is $(C_1\text{-}C_6)$-alkyl which may be substituted by $(C_3\text{-}C_7)$-cycloalkyl or once to three times by fluorine, or phenyl which may be substituted by halogen, cyano, $(C_1\text{-}C_4)$-alkyl, trifluoromethyl, $(C_1\text{-}C_4)$-alkoxy or trifluoromethoxy, or $(C_3\text{-}C_7)$-cycloalkyl,
  and
  $R^{15}$ is $(C_1\text{-}C_6)$-alkyl which may be substituted by $(C_3\text{-}C_7)$-cycloalkyl or once to three times by fluorine, or $(C_3\text{-}C_7)$-cycloalkyl,
$R^2$ is $(C_1\text{-}C_4)$-alkyl, trifluoromethyl, cyclopropyl, cyclobutyl, $(C_1\text{-}C_4)$-alkoxy or $(C_1\text{-}C_4)$-alkylthio,
and
$R^3$ is $(C_1\text{-}C_6)$-alkyl, $(C_1\text{-}C_6)$-alkoxy, trifluoromethoxy, $(C_1\text{-}C_6)$-alkylthio, amino, mono-$(C_1\text{-}C_6)$-alkylamino or a group of the formula —O—$SO_2$—$R^{16}$,
  where said $(C_1\text{-}C_6)$-alkyl, $(C_1\text{-}C_6)$-alkoxy and $(C_1\text{-}C_6)$-alkylthio radicals may in each case be substituted by $(C_3\text{-}C_7)$-cycloalkyl,
  and
  $R^{16}$ is $(C_1\text{-}C_6)$-alkyl, trifluoromethyl, $(C_3\text{-}C_7)$-cycloalkyl, phenyl or 5- or 6-membered heteroaryl having up to two heteroatoms from the series N, O and/or S,
    it being possible for phenyl and heteroaryl in turn each to be substituted once or twice, identically or differently, by halogen, cyano, nitro, $(C_1\text{-}C_4)$-alkyl, trifluoromethyl, $(C_1\text{-}C_4)$-alkoxy and/or trifluoromethoxy,
and the salts, solvates and solvates of the salts thereof.

Compounds of the invention are the compounds of the formula (I) and the salts, solvates and solvates of the salts thereof; the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds of the invention may occur in tautomeric forms, the present invention encompasses all tautomeric forms.

Salts which are preferred for the purposes of the present invention are physiologically acceptable salts of the compounds of the invention. Also encompassed are salts which are themselves unsuitable for pharmaceutical uses but can be used for example for isolating or purifying the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds of the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds of the invention (for example by metabolism or hydrolysis).

In the context of the present invention, the substituents have the following meaning, unless specified otherwise:

$(C_1-C_6)$-Alkyl, $(C_1-C_4)$-alkyl and $(C_1-C_3)$-alkyl represent in the context of the invention a straight-chain or branched alkyl radical having respectively 1 to 6, 1 to 4 and 1 to 3 carbon atoms. A straight-chain or branched alkyl radical having 1 to 4, particularly preferably having 1 to 3, carbon atoms is preferred. Mention may be made by way of example and preferably of: methyl, ethyl, n-propyl, isopropyl, n-butyl, iso-butyl, sec-butyl, tert-butyl, 1-ethylpropyl, n-pentyl, iso-pentyl and n-hexyl.

$(C_3-C_7)$-Cycloalkyl, $(C_3-C_6)$-cycloalkyl and $(C_3-C_5)$-cycloalkyl represent in the context of the invention a saturated monocyclic cycloalkyl group having respectively 3 to 7, 3 to 6 and 3 to 5 carbon atoms. Preference is given to a cycloalkyl radical having 3 to 6, particularly preferably having 3 to 5, carbon atoms. Mention may be made by way of example and preferably of: cyclopropyl, cyclobutyl, cyclopentyl, cyclohexyl and cycloheptyl.

$(C_1-C_6)$-Alkoxy, $(C_1-C_4)$-alkoxy and $(C_1-C_3)$-alkoxy represent in the context of the invention a straight-chain or branched alkoxy radical having respectively 1 to 6, 1 to 4 and 1 to 3 carbon atoms. A straight-chain or branched alkoxy radical having 1 to 4, particularly preferably having 1 to 3, carbon atoms is preferred. Mention may be made by way of example and preferably of: methoxy, ethoxy, n-propoxy, isopropoxy, n-butoxy, tert-butoxy, n-pentoxy and n-hexoxy.

$(C_1-C_6)$-Alkylthio and $(C_1-C_4)$-alkylthio represent in the context of the invention a straight-chain or branched alkylthio radical having respectively 1 to 6 and 1 to 4 carbon atoms. A straight-chain or branched alkylthio radical having 1 to 4 carbon atoms is preferred. Mention may be made by way of example and preferably of: methylthio, ethylthio, n-propylthio, isopropylthio, n-butylthio, tert-butylthio, n-pentylthio and n-hexylthio.

Mono-$(C_1-C_6)$-alkylamino and mono-$(C_1-C_4)$-alkylamino represent in the context of the invention an amino group having one straight-chain or branched alkyl substituent which has respectively 1 to 6 and 1 to 4 carbon atoms. A straight-chain or branched monoalkylamino radical having 1 to 4 carbon atoms is preferred. Mention may be made by way of example and preferably of: methylamino, ethylamino, n-propylamino, isopropylamino, n-butylamino, tert-butylamino, n-pentylamino and n-hexylamino.

Di-$(C_1-C_6)$-alkylamino and di-$(C_1-C_6)$-alkylamino represent in the context of the invention an amino group having two identical or different straight-chain or branched alkyl substituents, each of which have respectively 1 to 6 and 1 to 4 carbon atoms. Preference is given to straight-chain or branched dialkylamino radicals each having 1 to 4 carbon atoms. Mention may be made by way of example and preferably of: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

5- or 6-membered heteroaryl represents in the context of the invention an aromatic heterocycle (heteroaromatic) having 5 or 6 ring atoms which comprises one or two ring atoms from the series N, O and/or S and is linked via a ring carbon atom. Mention may be made by way of example and preferably of: furyl, pyrrolyl, thienyl, pyrazolyl, imidazolyl, thiazolyl, oxazolyl, isoxazolyl, isothiazolyl, pyridyl, pyrimidinyl, pyridazinyl and pyrazinyl.

Halogen includes in the context of the invention fluorine, chlorine, bromine and iodine. Fluorine or chlorine are preferred.

If radicals in the compounds of the invention are substituted, the radicals may be substituted one or more times, unless specified otherwise. In the context of the present invention, all radicals which occur more than once have a mutually independent meaning. Substitution by one, two or three identical or different substituents is preferred. Substitution by one substituent is very particularly preferred.

Preference is given to compounds of the formula (I) in which

D is N or C—$R^4$ in which
  $R^4$ is hydrogen, $(C_1-C_4)$-alkyl, $(C_1-C_4)$-alkoxy, $(C_1-C_4)$-alkylthio, amino, mono-$(C_1-C_4)$-alkylamino or di-$(C_1-C_4)$-alkylamino, E is N or C—$R^5$ in which $R^5$ is hydrogen or methyl,
where either D is C—$R^4$ and E is N or D is N and E is C—$R^5$,
Ar is a group of the formula

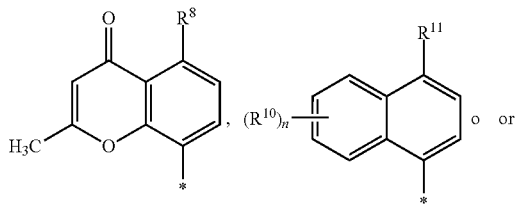

in which
* is the linkage point,
$R^8$ is hydrogen, fluorine, chlorine or cyano,
$R^{10}$ is fluorine, chlorine, methyl or ethyl,
$R^{11}$ is cyano or nitro,
$R^{12}$ is chlorine, bromine, $(C_1$-$C_4)$-alkyl, trifluoromethyl, $(C_1$-$C_4)$-alkoxy, trifluoromethoxy, $(C_1$-$C_4)$-alkylthio or trifluoromethylthio,
and
n is the number 0 or 1,
$R^1$ is cyano, acetyl, trifluoroacetyl or a group of the formula —C(=O)—O—$R^{15}$ in which
$R^{15}$ is $(C_1$-$C_4)$-alkyl which may be substituted by $(C_3$-$C_5)$-cycloalkyl or once to three times by fluorine, or $(C_3$-$C_5)$-cycloalkyl,
$R^2$ is methyl or trifluoromethyl,
and
$R^3$ is amino, $(C_1$-$C_4)$-alkoxy, trifluoromethoxy or a group of the formula —O—SO₂—$R^{16}$ in which
$R^{16}$ is $(C_1$-$C_4)$-alkyl, trifluoromethyl, $(C_3$-$C_6)$-cyaloalkyl, phenyl or thienyl,
where phenyl and thienyl in turn may each be substituted once or twice, identically or differently by fluorine, chlorine, cyano, methyl, trifluoromethyl, methoxy and/or trifluoromethoxy,
and the salts, solvates and solvates of the salts thereof.
Particular preference is given to compounds of the formula (I) in which
D is C—$R^4$ in which
$R^4$ is hydrogen, amino, methoxy or methylthio,
E is N,
Ar is a group of the formula

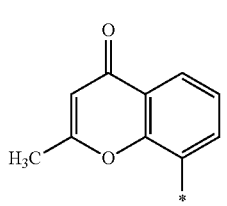 or 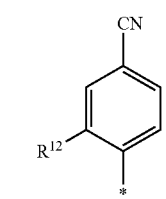

in which
* is the linkage point
and
$R^{12}$ is ethyl, methoxy or trifluoromethoxy,
$R^1$ is cyano, acetyl, methoxycarbonyl or ethoxycarbonyl,
$R^2$ is methyl or trifluoromethyl,
and
$R^3$ is amino, $(C_1$-$C_3)$-alkoxy or a group of the formula —O—SO₂—$R^{16}$ in which
$R^{16}$ is $(C_1$-$C_3)$-alkyl,
and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I-A)

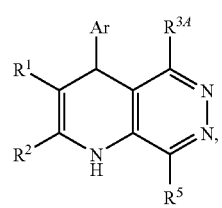
(I-A)

in which Ar, $R^1$, $R^2$ and $R^5$ each have the meanings indicated above,
and
$R^{3A}$ is $(C_1$-$C_6)$-alkoxy, which may be substituted by $(C_3$-$C_7)$-cycloalkyl, is trifluoromethoxy or is a group of the formula —O—SO₂—$R^{16}$ in which $R^{16}$ has the meaning indicated above,
characterized in that a compound of the formula (II)

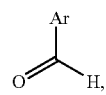
(II)

in which Ar has the meaning indicated above,
is reacted in a one-stage (one-pot reaction) or two-stage process with a compound of the formula (III)

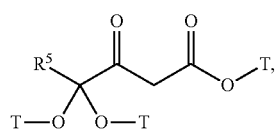
(III)

in which $R^5$ has the meaning indicated above
and
T is methyl or ethyl,
and a compound of the formula (IV)

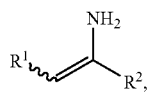
(IV)

in which $R^1$ and $R^2$ have the meanings indicated above,
to give a compound of the formula (V)

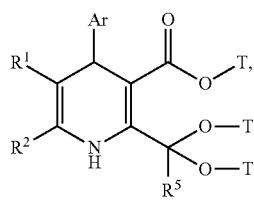
(V)

in which Ar, $R^1$, $R^2$, $R^5$ and T each have the meanings indicated above,
the latter is hydrolyzed in the presence of an acid to give a compound of the formula (VI)

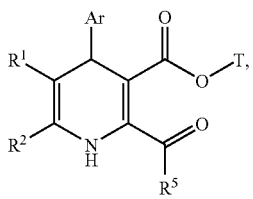
(VI)

in which Ar, $R^1$, $R^2$, $R^5$ and T each have the meanings indicated above,
then condensed with hydrazine in the presence of an acid to give a compound of the formula (VII)

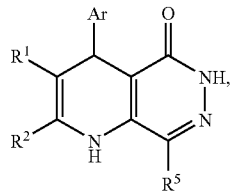
(VII)

in which Ar, $R^1$, $R^2$ and $R^5$ each have the meanings indicated above,
and then alkylated in an inert solvent, where appropriate in the presence of a base, with a compound of the formula (VIII) or a trialkyloxonium salt of the formula (IX)

$R^{17}$—Q (VIII)

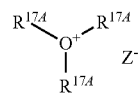
(IX)

in which
$R^{17}$ is $(C_1-C_6)$-alkyl which may be substituted by $(C_3-C_7)$-cycloalkyl or is trifluoromethyl,
$R^{17A}$ is methyl or ethyl,
Q is a leaving group such as, for example, halogen, mesylate, tosylate or triflate,
and
$Z^-$ is a non-nucleophilic anion such as, for example, tetrafluoroborate, to give compounds of the formula (I-A1)

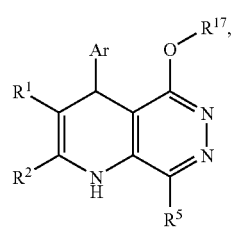
(I-A1)

in which Ar, $R^1$, $R^2$, $R^5$ and $R^{17}$ each have the meanings indicated above,
or the compounds of the formula (VII) are reacted in an inert solvent in the presence of a base with a compound of the formula (X)

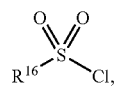
(X)

in which $R^{16}$ has the meaning indicated above,
to give compounds of the formula (I-A2)

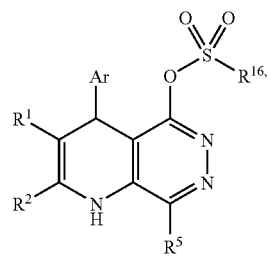
(I-A2)

in which Ar, $R^1$, $R^2$, $R^5$ and $R^{16}$ each have the meanings indicated above,
and where appropriate the resulting compounds of the formula (I-A1) or (I-A2) are separated by methods known to the skilled worker into their enantiomers and/or diastereomers, and/or converted with the appropriate (i) solvents and/or (ii) bases or acids into the solvates, salts and/or solvates of the salts thereof.

Process step (II)+(III)+(IV)→(V) is generally carried out in an inert solvent in a temperature range from +20° C. to the boiling point of the solvent under atmospheric pressure.

Inert solvents suitable for this purpose are for example alcohols such as methanol, ethanol, n-propanol, isopropanol, n-butanol or tert-butanol, halohydrocarbons such as dichloromethane, trichloromethane, tetrachloromethane, trichloroethane or 1,2-dichloroethane, or other solvents such as acetonitrile, tetrahydrofuran, dioxane, 1,2-dimethoxyethane, hexane, benzene, toluene, xylene, chlorobenzene, pyridine or glacial acetic acid. The reactions are preferably carried out in dichloromethane, toluene, ethanol or isopropanol at the respective reflux temperature under atmospheric pressure.

Process step (II)+(III)+(IV)→(V) can where appropriate advantageously take place in the presence of an acid, of an acid/base combination and/or of a dehydrating agent such as, for example, molecular sieves. Examples of suitable acids are acetic acid, trifluoroacetic acid, methanesulfonic acid or p-toluenesulfonic acid; suitable bases are in particular piperidine or pyridine [compare reaction scheme 8 hereinafter; for the synthesis of 1,4-dihydropyridines, compare also D. M. Stout, A. I. Meyers, *Chem. Rev.* 1982, 82, 223-243; H. Meier et al., *Liebigs Ann. Chem.* 1977, 1888; H. Meier et al., *ibid.* 1977, 1895; H. Meier et al., ibid. 1976, 1762; F. Bossert et al., *Angew. Chem.* 1981, 93, 755].

Process step (V)→(VI) is expediently carried out in water in conjunction with a water-miscible, inert organic solvent such as acetone, tetrahydrofuran, dioxane or acetic acid; acetone is preferably employed. Acids suitable for this hydrolysis are dilute aqueous solutions of mineral acids such as, for example, hydrochloric acid, hydrobromic acid, sulfuric acid, nitric acid or phosphoric acid, or of organic acids such as acetic acid, trifluoroacetic acid, methanesulfonic acid or trifluoromethanesulfonic acid; hydrochloric acid is preferably used.

The reaction (V)→(VI) generally takes place in a temperature range from 0° C. to +50° C. The reaction can be carried out under atmospheric, elevated or reduced pressure (e.g. from 0.5 to 5 bar). It is generally carried out under atmospheric pressure.

Inert solvents for process step (VI)→(VII) are for example alcohols such as methanol, ethanol, n-propanol, isopropanol, n-butanol or tert-butanol, ethers such as diethyl ether, methyl tert-butyl ether, dioxane, tetrahydrofuran, glycol dimethyl ether or diethylene glycol dimethyl ether, hydrocarbons such as benzene, toluene or xylene, halohydrocarbons such as dichloromethane, trichloromethane, tetrachloromethane, 1,2-dichloroethane, trichloroethane, tetrachloroethane, trichloroethylene, chlorobenzene or chlorotoluene, or other solvents such as acetonitrile, acetic acid, N,N-dimethylformamide (DMF), dimethyl sulfoxide (DMSO), N,N'-dimethylpropyleneurea (DMPU) or N-methylpyrrolidone (NMP). It is likewise possible to use mixtures of the solvents mentioned. Ethanol is preferably employed.

Acids suitable for process step (VI)→(VII) are in particular organic acids such as acetic acid, trifluoroacetic acid, methanesulfonic acid, trifluoromethanesulfonic acid or p-toluenesulfonic acid; acetic acid is preferably used.

The reaction (VI)→(VII) generally takes place in a temperature range from +20° C. to +150° C., preferably at +60° C. to +120° C. The reaction can be carried out under atmospheric, elevated or reduced pressure (e.g. from 0.5 to 5 bar). It is generally carried out under atmospheric pressure.

Inert solvents for process steps (VII)+(VIII)→(I-A1), (VII)+(IX)→(I-A1) and (VII)+(X)→(I-A2) are for example ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethane, tetrachloroethane, trichloroethylene, chlorobenzene or chlorotoluene, or other solvents such as N,N-dimethylformamide (DMF), dimethyl sulfoxide (DMSO), N,N'-dimethylpropyleneurea (DMPU), N-methylpyrrolidone (NMP), pyridine or acetonitrile. It is likewise possible to use mixtures of said solvents. Preference is given to the use of tetrahydrofuran or dimethylformamide in process step (VII)+(VIII)→(I-A1), of dichloromethane in process step (VII)+(IX)→(I-A1), and of pyridine in process step (VII)+(X)→(I-A2).

Bases suitable for process step (VII)+(VIII)→(I-A1) are in particular alkali metal or alkaline earth metal carbonates such as lithium, sodium, potassium, calcium or cesium carbonate, alkali metal hydrides such as sodium or potassium hydride, amides such as lithium, sodium or potassium bis(trimethylsilyl)amide or lithium diisopropylamide, organometallic compounds such as butyllithium or phenyllithium, or else phosphazene bases such as, for example, P2-t-Bu or P4-t-Bu [so-called "Schwesinger bases", compare R. Schwesinger, H. Schlemper, *Angew. Chem. Int. Ed. Engl.* 26, 1167 (1987); T. Pietzonka, D. Seebach, *Chem. Ber.* 124, 1837 (1991)]. Sodium hydride or the phosphazene base P4-t-Bu is preferably used.

Bases suitable for process step (VII)+(X)→(I-A2) are in particular alkali metal or alkaline earth metal carbonates such as lithium, sodium, potassium, calcium or cesium carbonate, alkali metal hydrides such as sodium or potassium hydride, organometallic compounds such as butyllithium or phenyllithium, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo-[5.4.0]undec-7-ene (DBU) or 1,4-diazabicyclo[2.2.2]octane (DABCO®). Pyridine is preferably used and simultaneously also serves as solvent.

Process step (VII)+(IX)→(I-A1) is generally carried out without addition of a base.

The reactions (VII)+(VIII)→(I-A1), (VII)+(IX)→(I-A1) and (VII)+(X)→(I-A2) generally take place in a temperature range from −20° C. to +100° C., preferably at 0° C. to +50° C. The reactions can be carried out under atmospheric, elevated or reduced pressure (e.g. from 0.5 to 5 bar); they are generally carried out under atmospheric pressure.

The compounds of the formula (II) are commercially available, known from the literature or can be prepared in analogy to processes known from the literature (compare reaction schemes 1-7 hereinafter). The compounds of the formulae (III), (IV), (VIII), (IX) and (X) are in many cases commercially available, known from the literature or can be prepared by methods known from the literature.

The invention further relates to a process for preparing the compounds of the invention of the formula (I-B)

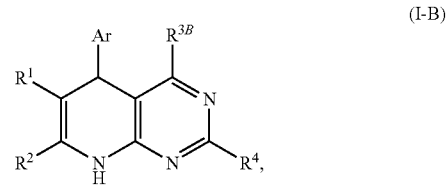

in which Ar, $R^1$, $R^2$ and $R^4$ each have the meanings indicated above,
and
$R^3B$ is $(C_1-C_6)$-alkoxy or $(C_1-C_6)$-alkylthio, each of which may be substituted by $(C_3-C_7)$-cycloalkyl, or is trifluoromethoxy, amino, mono-$(C_1-C_6)$-alkylamino or a group of the formula —O—SO$_2$—R$^{16}$ in which R$^{16}$ has the meaning indicated above, characterized in that a compound of the formula (II)

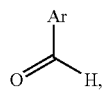
(II)

in which Ar has the meaning indicated above,
is condensed with a compound of the formula (XI)

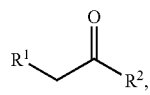
(XI)

in which R$^1$ and R$^2$ have the meanings indicated above,
to give a compound of the formula (XII)

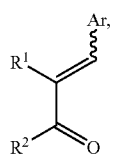
(XII)

in which Ar, R$^1$ and R$^2$ each have the meanings indicated above,
and the latter is subsequently either

[B-1] reacted in an inert solvent with a compound of the formula (XIII)

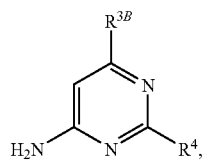
(XIII)

in which R$^{3B}$ and R$^4$ have the meanings indicated above,
or
[B-2] is initially reacted in an inert solvent with a compound of the formula (XIV)

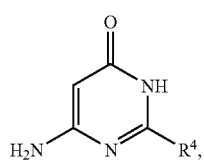
(XIV)

in which R$^4$ has the meaning indicated above,
to give a compound of the formula (XV)

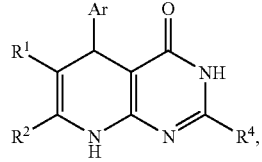
(XV)

in which Ar, R$^1$, R$^2$ and R$^4$ each have the meanings indicated above, and the latter is then alkylated in an inert solvent, where appropriate in the presence of a base, with a compound of the formula (VIII) or a trialkyloxonium salt of the formula (IX)

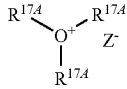
(VIII)

(IX)

in which

R$^{17}$ is $(C_1-C_6)$-alkyl which may be substituted by $(C_3-C_7)$-cycloalkyl, or is trifluoromethyl, R$^{17A}$ is methyl or ethyl, Q is a leaving group such as, for example, halogen, mesylate, tosylate or triflate, and Z$^-$ is a non-nucleophilic anion, such as, for example, tetrafluoroborate, to give compounds of the formula (I-B1)

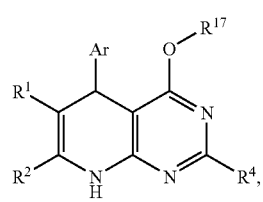
(I-B1)

in which Ar, R$^1$, R$^2$, R$^4$ and R$^{17}$ each have the meanings indicated above, or the compounds of the formula (XV) are reacted in an inert solvent in the presence of a base with a compound of the formula (X)

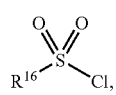
(X)

in which R$^{16}$ has the meaning indicated above,
to give compounds of the formula (I-B2)

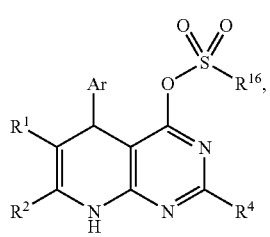

(I-B2)

in which Ar, $R^1$, $R^2$, $R^4$ and $R^{16}$ each have the meanings indicated above, and where appropriate the respective resulting compounds of the formula (I-B), (I-B1) or (I-B2) are separated by methods known to the skilled worker into their enantiomers and/or diastereomers, and/or converted with the appropriate (i) solvents and/or (ii) bases or acids into the solvates, salts and/or solvates of the salts thereof.

Process step (II)+(XI)→(XII) generally takes place in an inert solvent, where appropriate in the presence of an acid and/or base, in a temperature range from +20° C. to the boiling point of the solvent under atmospheric pressure.

Inert solvents suitable in this case are for example halohydrocarbons such as dichloromethane, trichloromethane, tetrachloromethane, trichloroethane or 1,2-dichloroethane, or other solvents such as acetonitrile, glacial acetic acid, pyridine, benzene, chlorobenzene, toluene or xylene. The reaction preferably takes place in dichloromethane or toluene at the particular reflux temperature under atmospheric pressure.

The reaction (II)+(XI)→(XII) is advantageously carried out in the presence of an acid in combination with piperidine or pyridine as base and/or with a dehydrating agent such as, for example, molecular sieves. Suitable acids are for example acetic acid or p-toluenesulfonic acid. The reaction is preferably carried out with addition of piperidinium acetate.

Inert solvents for process steps (XII)+(XIII)→(I-B) and (XII)+(XIV)→(XV) are for example alcohols such as methanol, ethanol, n-propanol, isopropanol, n-butanol or tert-butanol, or other solvents such as acetonitrile, tetrahydrofuran, dioxane, 1,2-dimethoxyethane, toluene or glacial acetic acid. The reactions generally take place in a temperature range from +50° C. to +120° C. The reactions are preferably carried out in ethanol or isopropanol at the particular reflux temperature under atmospheric pressure.

Inert solvents for process steps (XV)+(VIII)→(I-B1), (XV)+(IX)→(I-B1) and (XV)+(X)→(I-B2) are for example ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethane, tetrachloroethane, trichloroethylene, chlorobenzene or chlorotoluene, or other solvents such as N,N-dimethylformamide (DMF), dimethyl sulfoxide (DMSO), N,N'-dimethylpropyleneurea (DMPU), N-methylpyrrolidone (NMP), pyridine or acetonitrile. It is likewise possible to use mixtures of the solvents mentioned. Preference is given to the use of tetrahydrofuran or dimethylformamide in process step (XV)+(VIII)→(I-B1), of dichloromethane in process step (XV)+(IX)→(I-B1), and of pyridine in process step (XV)+(X)→(I-B2).

Bases suitable for process step (XV)+(VIII)→(I-B1) are in particular alkali metal or alkaline earth metal carbonates such as lithium, sodium, potassium, calcium or cesium carbonate, alkali metal hydrides such as sodium or potassium hydride, amides such as lithium, sodium or potassium bis(trimethylsilyl)amide or lithiumdiisopropylamide, organometallic compounds such as butyllithium or phenyllithium, or else phosphazene bases such as, for example, P2-t-Bu or P4-t-Bu [so-called "Schwesinger bases", cf. R. Schwesinger, H. Schlemper, Angew. Chem. Int. Ed. Engl. 26, 1167 (1987); T. Pietzonka, D. Seebach, Chem. Ber. 124, 1837 (1991)]. Sodium hydride or the phosphazene base P4-t-Bu is preferably used.

Bases suitable for process step (XV)+(X)→(I-B2) are in particular alkali metal or alkaline earth metal carbonates such as lithium, sodium, potassium, calcium or cesium carbonate, alkali metal hydrides such as sodium or potassium hydride, organometallic compounds such as butyllithium or phenyllithium, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo-[5.4.0]undec-7-ene (DBU) or 1,4-diazabicyclo[2.2.2]octane (DABCO ). Pyridine is preferably used and simultaneously acts as solvent.

Process step (XV)+(IX)→(I-B1) is generally carried out without addition of a base.

The reactions (XV)+(VIII)→(I-B1), (XV)+(IX)→(I-B1) and (XV)+(X)→(I-B2) generally take place in a temperature range from −20° C. to +100° C., preferably at 0° C. to +50° C. The reactions can be carried out under atmospheric, elevated or reduced pressure (e.g. from 0.5 to 5 bar). They are generally carried out under atmospheric pressure.

The compounds of the formula (II) are commercially available, known from the literature or can be prepared in analogy to processes known from the literature (cf. reaction schemes 1-7 below). The compounds of the formulae (XIII) and (XIV) are in some cases commercially available or else known from the literature or can be prepared by literature processes (cf. reaction scheme 9 and literature cited therein).

The compounds of the formulae (VIII), (IX), (X) and (XI) are in many cases commercially available, known from the literature or can be prepared by methods known from the literature.

Preparation of the compounds of the invention can be illustrated by the following synthesis schemes:

Scheme 1

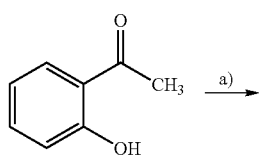

a)

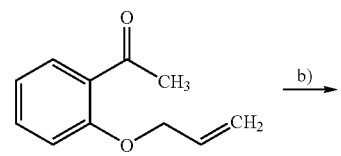

b)

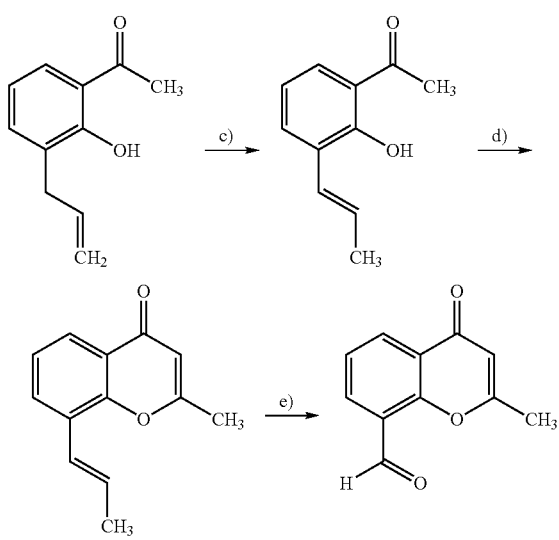
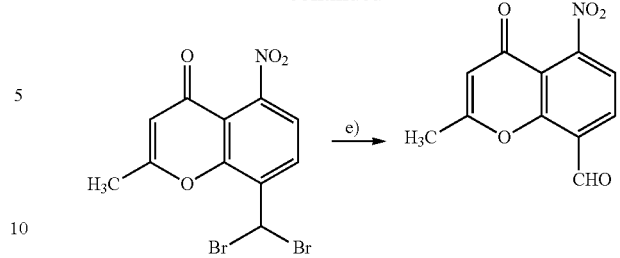
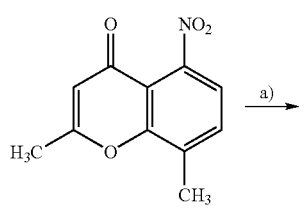
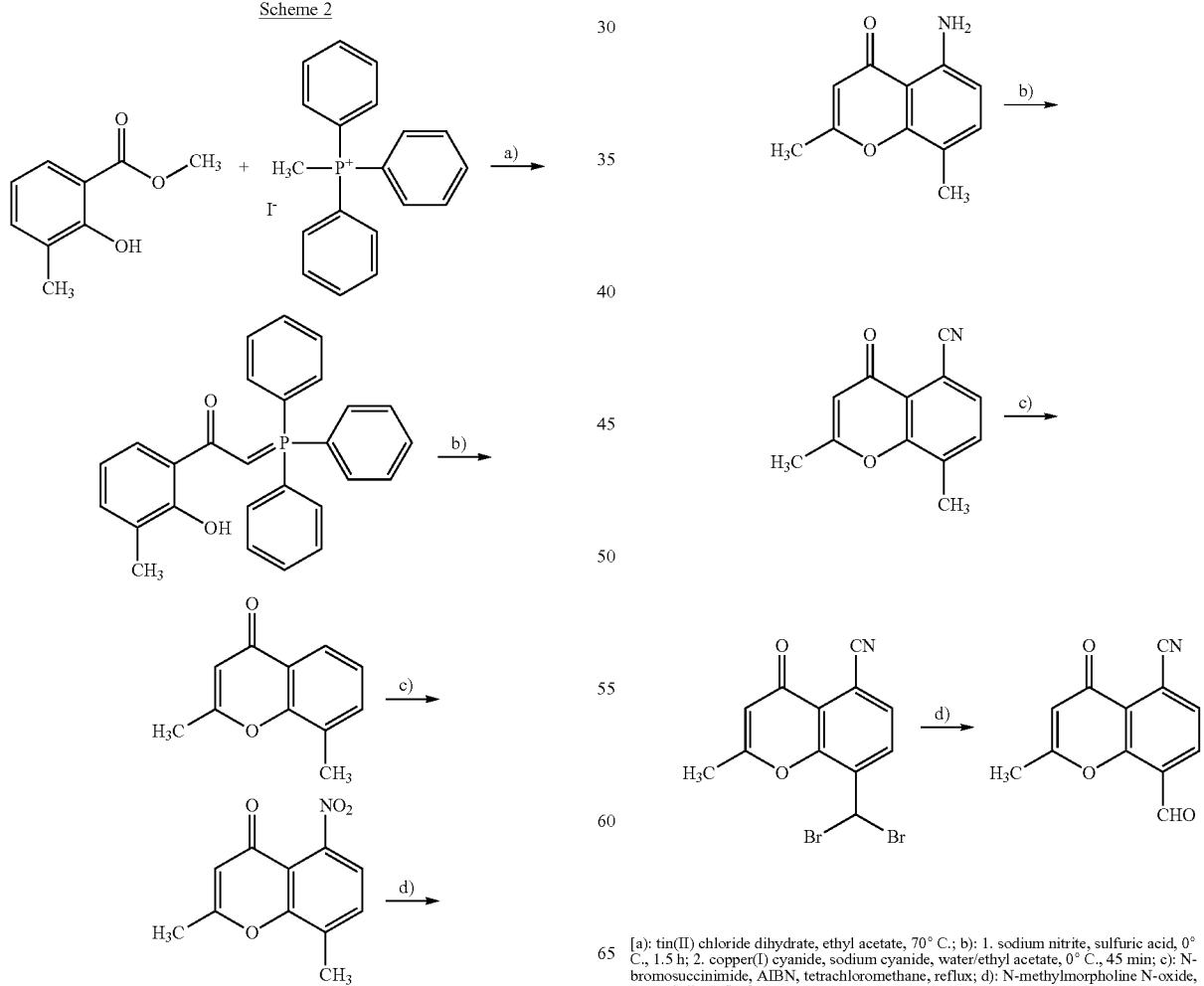

Scheme 4

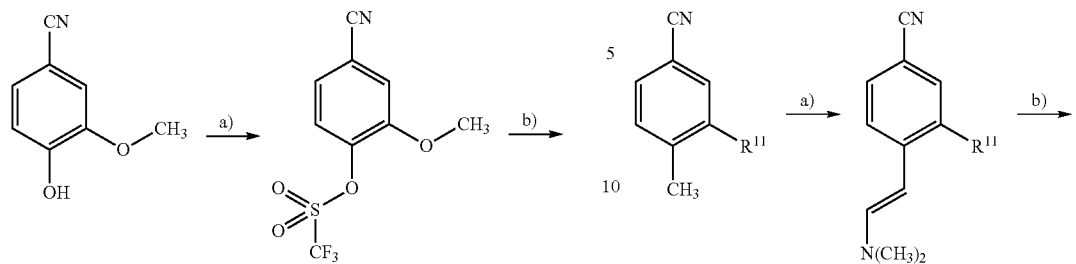

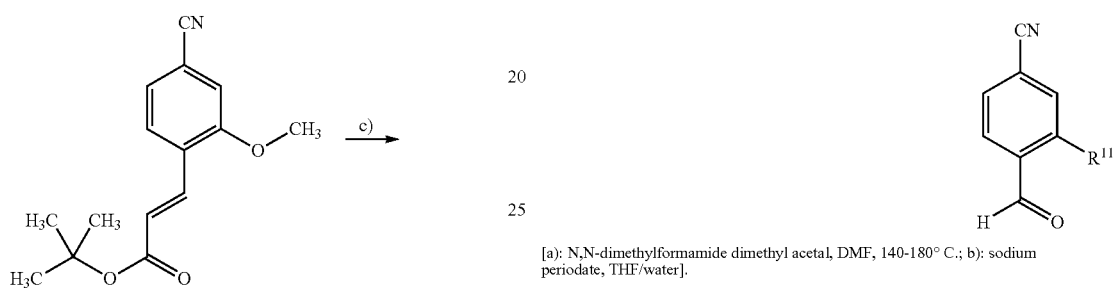

[a]: trifluoromethanesulfonic anhydride, pyridine, 0° C. → RT, 30 min; b): tert-butyl acrylate, bis(triphenylphosphine)dichloropalladium(II), DMF, 120° C., 24 h; c): cat. osmium tetroxide, cat. benzyltriethylammonium chloride, sodium periodate, THF/water, 20-25° C., 2 h].

Scheme 5

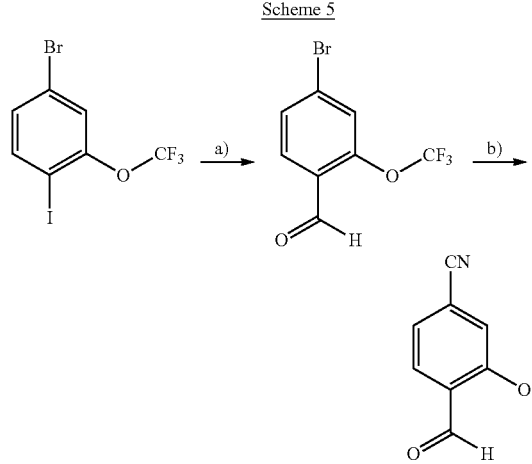

[a]: n-butyllithium, THF, -78° C., then N-formylmorpholine; b): zinc cyanide, tetrakis(triphenyl-phosphine)palladium(0), DMF, microwave 250° C./5 min].

Scheme 6

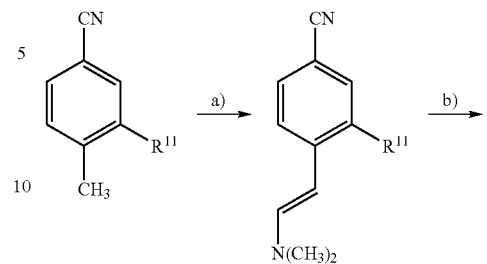

[a]: N,N-dimethylformamide dimethyl acetal, DMF, 140-180° C.; b): sodium periodate, THF/water].

Scheme 7

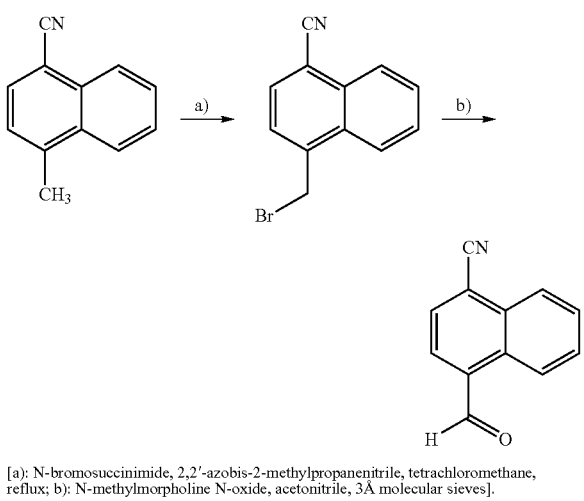

[a]: N-bromosuccinimide, 2,2'-azobis-2-methylpropanenitrile, tetrachloromethane, reflux; b): N-methylmorpholine N-oxide, acetonitrile, 3Å molecular sieves].

Scheme 8

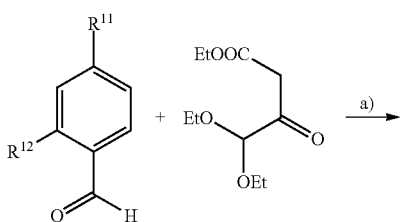

-continued

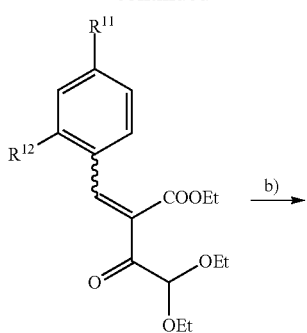

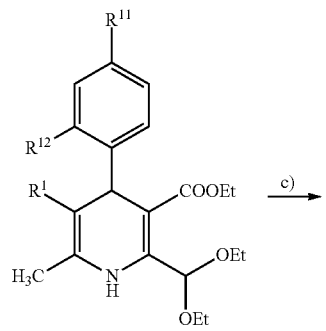

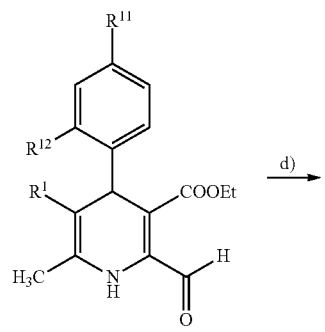

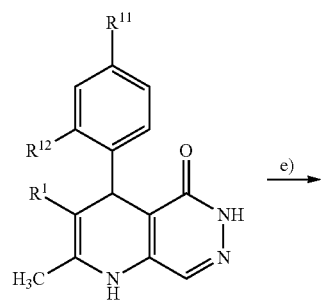

-continued

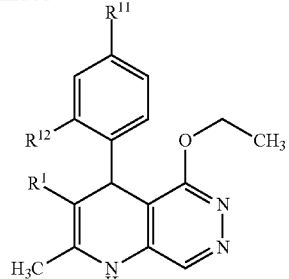

[a]: Acetic acid, piperidine, dichloromethane, reflux; b): 4-amino-3-penten-2-one ($R^1 = CH_3\text{—}CO\text{—}$) or ethyl 3-aminobut-2-enoate ($R^1 = EtOOC\text{—}$), isopropanol, reflux; c): hydrochloric acid, acetone, RT; d): hydrazine hydrate, ethanol/acetic acid, 100° C.; e): triethyloxonium tetrafluoroborate, dichloromethane, RT].

Scheme 9

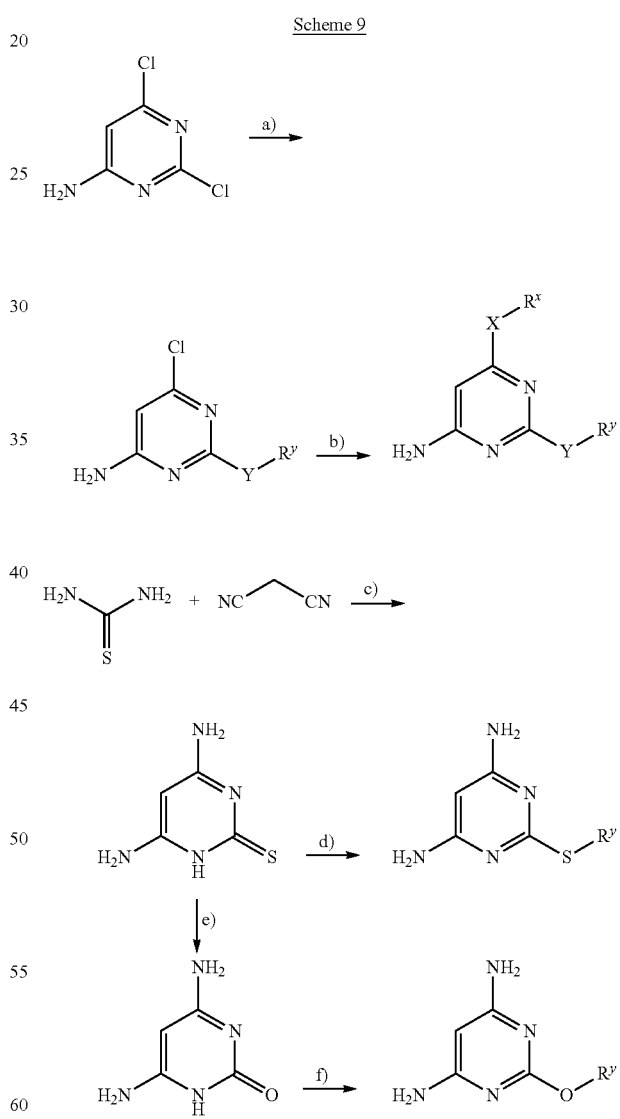

[X, Y = N, O or S; a): $R^y$—YH, base; cf., for example, R.A. Nugent et al., *J. Med. Chem.* 1998, 41, 3793-3803. b): $R^x$—XH, base; cf., for example P. Manesiotis et al., *J. Org. Chem.* 2005, 70, 2729-2738 (X = N); B. Roth et al., *J. Am. Chem. Soc.* 1951, 73, 2864-2868 (X = O). c): NaOEt, EtOH; see A. Bendich et al., *J. Am. Chem. Soc.* 1948, 70, 3109-3113. d): $R^y$—I, EtOH or $R^y$—I, $K_2CO_3$, acetone; cf., for example, E.C. Taylor, C.K. Cain, *J. Am. Chem. Soc.* 1952, 74, 1644-1647. e): chloroacetic acid, sulfuric acid; cf., for example, A. Bendich et al., *J. Am. Chem. Soc.* 1948, 70, 3109-3113. f): $(R^y)_3O^+BF_4^-$, dichloromethane].

Scheme 10

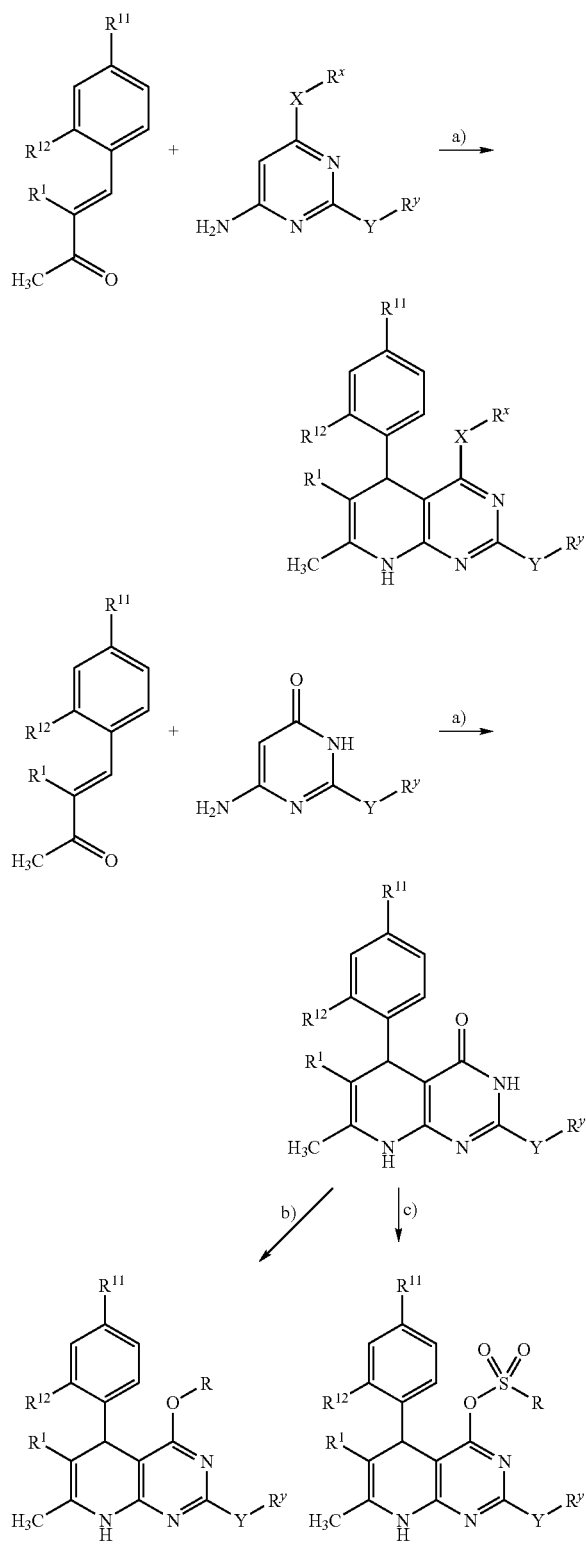

[X, Y = N, O or S; a): isopropanol, reflux, 12 h; b): R₃O⁺BF₄⁻, dichloromethane, RT, 2-12 h; c): R—SO₂—Cl, pyridine, RT, 1-3 h].

The compounds of the invention act as antagonists of the mineralocorticoid receptor and show a valuable range of pharmacological effects which could not have been predicted. They are therefore suitable for use as medicaments for the treatment and/or prophylaxis of diseases in humans and animals.

The compounds of the invention are suitable for the prophylaxis and/or treatment of various disorders and disease-related conditions, especially of disorders which are characterized either by an elevation of the plasma aldosterone concentration or by a change in the plasma aldosterone concentration relative to the plasma renin concentration, or are associated with these changes. Examples which may be mentioned are: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The compounds of the invention are also suitable, because of their mechanism of action, for the prophylaxis of sudden cardiac death in patients at increased risk of dying of sudden cardiac death. These are in particular patients suffering for example from one of the following disorders: hypertension, heart failure, coronary heart disease, stable and unstable angina pectoris, myocardial ischemia, myocardial infarction, dilated cardiomyopathies, shock, arteriosclerosis, atrial and ventricular arrhythmia, transient and ischemic attacks, stroke, inflammatory cardiovascular disorders, peripheral and cardiac vascular disorders, peripheral blood flow disturbances, pulmonary hypertension, spasms of the coronary arteries and peripheral arteries, thromboses, thromboembolic disorders, and vasculitis.

The compounds of the invention can additionally be used for the prophylaxis and/or treatment of edema formation, such as, for example, pulmonary edema, renal edema or heart failure-related edema, and of restenoses such as following thrombolysis therapies, percutaneous transluminal angioplasties (PTA) and transluminal coronary angioplasties (PTCA), heart transplants and bypass operations.

The compounds of the invention are further suitable for use as diuretic and for electrolyte disturbances such as, for example, hypercalcemia.

The compounds of the invention can additionally be employed for the prophylaxis and/or treatment of diabetes mellitus and diabetic sequelae such as, for example, neuropathy and nephropathy, of acute and chronic renal failure and chronic renal insufficiency.

The present invention further relates to the use of the compounds of the invention for the treatment and/or prevention of disorders, especially of the aforementioned disorders.

The present invention further relates to the use of the compounds of the invention for the manufacture of a medicament for the treatment and/or prevention of disorders, especially of the aforementioned disorders.

The present invention further relates to a method for the treatment and/or prevention of disorders, especially of the aforementioned disorders, by using an effective amount of at least one of the compounds of the invention.

The compounds of the invention can be employed alone or, if required, in combination with other active ingredients. The present invention further relates to medicaments comprising at least one of the compounds of the invention and one or more further active ingredients, especially for the treatment and/or prevention of the aforementioned disorders. Suitable active ingredients for combinations are by way of example and preferably:

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers and Rho kinase inhibitors;

diuretics, especially loop diuretics, and thiazides and thiazide-like diuretics;

agents having an antithrombotic effect, for example and preferably from the group of platelet aggregation inhibitors, of anticoagulants or of profibrinolytic substances;

active ingredients which alter lipid metabolism, for example and preferably from the group of thyroid receptor agonists, cholesterol synthesis inhibitors such as by way of example and preferably HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists;

organic nitrates and NO donors such as, for example, sodium nitroprusside, nitroglycerin, isosorbide mononitrate, isosorbide dinitrate, molsidomine or SIN-1, and inhaled NO;

compounds having a positive inotropic effect, such as, for example, cardiac glycosides (digoxin), beta-adrenergic and dopaminergic agonists such as isoproterenol, adrenaline, noradrenaline, dopamine and dobutamine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as amrinone and milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

calcium sensitizers such as by way of example and preferably levosimendan;

potassium supplements;

NO-independent but heme-dependent stimulators of guanylate cyclase such as in particular the compounds described in WO 00/06568, WO 00/06569, WO 02/42301 and WO 03/095451;

NO- and heme-independent activators of guanylate cyclase, such as in particular the compounds described in WO 01/19355, WO 01/19776, WO 01/19778, WO 01/19780, WO 02/070462 and WO 02/070510;

inhibitors of human neutrophil elastase (HNE), such as, for example, sivelestat or DX-890 (reltran);

compounds which inhibit the signal transduction cascade, such as, for example, tyrosine kinase inhibitors, in particular sorafenib, imatinib, gefitinib and erlotinib; and/or compounds which influence the energy metabolism of the heart, such as by way of example and preferably etomoxir, dichloroacetate, ranolazine or trimetazidine.

In a preferred embodiment of the invention, the compounds of the invention are administered in combination with a diuretic such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorophenamide, methazolamide, glycerol, isosorbide, mannitol, amiloride or triamterene.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, Rho kinase inhibitors, and diuretics.

In a preferred embodiment of the invention, the compounds of the invention are administered in combination with a calcium antagonist such as by way of example and preferably nifedipine, amlodipine, verapamil or diltiazem.

In a preferred embodiment of the invention, the compounds of the invention are administered in combination with an angiotensin AII antagonist such as by way of example and preferably losartan, candesartan, valsartan, telmisartan or embusartan.

In a preferred embodiment of the invention, the compounds of the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds of the invention are administered in combination with an endothelin antagonist such as by way of example and preferably bosentan, darusentan, ambrisentan or sitaxsentan.

In a preferred embodiment of the invention, the compounds of the invention are administered in combination with a renin inhibitor such as by way of example and preferably aliskiren, SPP-600 or SPP-800.

In a preferred embodiment of the invention, the compounds of the invention are administered in combination with an alpha-1 receptor blocker such as by way of example and preferably prazosin.

In a preferred embodiment of the invention, the compounds of the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with a Rho kinase inhibitor such as by way of example and preferably fasudil, Y-27632, SLx-2119, BF-6685 1, BF-66852, BF-66853, KI-23095 or BA-1049.

Agents having an antithrombotic effect (antithrombotics) preferably mean compounds from the group of platelet aggregation inhibitors, of anticoagulants or of profibrinolytic substances.

In a preferred embodiment of the invention, the compounds of the invention are administered in combination with a platelet aggregation inhibitor such as by way of example and preferably aspirin, clopidogrel, ticlopidine or dipyridamole.

In a preferred embodiment of the invention, the compounds of the invention are administered in combination with a thrombin inhibitor such as by way of example and preferably ximelagatran, melagatran, bivalirudin or clexane.

In a preferred embodiment of the invention, the compounds of the invention are administered in combination with a GPIIb/IIIa antagonist such as by way of example and preferably tirofiban or abciximab.

In a preferred embodiment of the invention, the compounds of the invention are administered in combination with a factor Xa inhibitor such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or a low molecular weight (LMW) heparin derivative.

In a preferred embodiment of the invention, the compounds of the invention are administered in combination with a vitamin K antagonist such as by way of example and preferably coumarin.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds of the invention are administered in combination with a CETP inhibitor such as by way of example and preferably torcetrapib (CP-529 414), JJT-705, BAY 60-5521, BAY 78-7499 or CETP vaccine (Avant).

In a preferred embodiment of the invention, the compounds of the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds of the invention are administered in combination with a squalene synthesis inhibitor such as by way of example and preferably BMS-188494 or TAK-475.

In a preferred embodiment of the invention, the compounds of the invention are administered in combination with an ACAT inhibitor such as by way of example and preferably avasimibe, melinamide, pactimibe, eflucimibe or SMP-797.

In a preferred embodiment of the invention, the compounds of the invention are administered in combination with an MTP inhibitor such as by way of example and preferably implitapide, BMS-201038, R-103757 or JTT-130.

In a preferred embodiment of the invention, the compounds of the invention are administered in combination with a PPAR-gamma agonist such as by way of example and preferably pioglitazone or rosiglitazone.

In a preferred embodiment of the invention, the compounds of the invention are administered in combination with a PPAR-delta agonist such as by way of example and preferably GW-501516 or BAY 68-5042.

In a preferred embodiment of the invention, the compounds of the invention are administered in combination with a cholesterol absorption inhibitor such as by way of example and preferably ezetimibe, tiqueside or pamaqueside.

In a preferred embodiment of the invention, the compounds of the invention are administered in combination with a lipase inhibitor such as by way of example and preferably orlistat.

In a preferred embodiment of the invention, the compounds of the invention are administered in combination with a polymeric bile adsorbent such as by way of example and preferably cholestyramine, colestipol, colesolvam, CholestaGel or colestimide.

In a preferred embodiment of the invention, the compounds of the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds of the invention are administered in combination with a lipoprotein(a) antagonist such as by way of example and preferably gemcabene calcium (CI-1027) or nicotinic acid.

The present invention further relates to medicaments which comprise at least one compound of the invention, normally together with one or more inert, non-toxic, pharmaceutically suitable excipients, and to the use thereof for the aforementioned purposes.

The compounds of the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral administration.

The compounds of the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

| Abbreviations and acronyms: | |
|---|---|
| abs. | absolute |
| cat. | catalytic |
| CI | chemical ionization (in MS) |
| conc. | concentrated |
| d | day(s) |
| DMF | dimethylformamide |
| DMSO | dimethyl sulfoxide |
| EI | electron impact ionization (in MS) |
| ent | enantiomer/enantiopure |
| eq | equivalent(s) |
| ESI | electrospray ionization (in MS) |
| Et | ethyl |
| GC-MS | coupled gas chromatography-mass spectrometry |
| h | hour(s) |
| HPLC | high pressure, high performance liquid chromatography |
| LC-MS | coupled liquid chromatography-mass spectrometry |
| min | minute(s) |
| MS | mass spectrometry |
| NMR | nuclear magnetic resonance spectrometry |
| $R_f$ | retention index (in TLC) |
| $R_t$ | retention time (in HPLC) |
| RT | room temperature |
| THF | tetrahydrofuran |
| TLC | thin-layer chromatography |
| v/v | volume-to-volume ratio (of a solution) |
| wt % | percent by weight |

LC-MS, GC-MS and HPLC Methods:

Method 1 (LC-MS):
MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS):
MS instrument type: Micromass ZQ; HPLC instrument type: HP 1100 Series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS):
Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 4 (LC-MS):
MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (LC-MS):
Instrument: Micromass Platform LCZ with HPLC Agilent Series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS):
Instrument: Micromass Platform LCZ with HPLC Agilent Series 1100; column: Thermo HyPURITY Aquastar 3μ 20 mm×2.1 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 7 (GC-MS):
Instrument: Micromass GCT, GC 6890; column: Restek RTX-35MS, 30 m×250 μm×0.25 μm; constant flow with helium: 0.88 ml/min; oven: 60° C.; inlet: 250° C.; gradient: 60° C. (halt for 0.30 min), 50° C./min→120° C., 16° C./min→250° C., 30° C./min→300° C. (halt for 1.7 min).

Method 8 (HPLC):
Instrument: HP 1100 with DAD detection; column: Kromasil 100 RP-18, 60 mm×2.1 mm, 3.5 μm; eluent A: 5 ml of $HClO_4$ (70%)/liter of water, eluent B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 9 (Chiral HPLC):
Column: 250 mm×46 mm, based on the chiral selector poly(N-methacryloyl-D-leucine tert-butylamide); eluent: isohexane/ethyl acetate 1:1; temperature: 24° C.; flow rate: 2 ml/min; UV detection: 260 nm.

Method 10 (Chiral HPLC):
Column: Daicel Chiralpak AD-H, 5 μm, 250 mm×4 mm; eluent: isohexane/isopropanol 80:20; temperature: 35° C.; flow rate: 2 ml/min; UV detection: 250 nm.

Method 11 (LC-MS):
Instrument: Micromass Quattro LCZ with HPLC Agilent Series 1100; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A;

flow rate: 0.0 min 1 ml/min→2.5 min/3.0 min/4.5 min 2 ml/min; oven: 50° C.; UV detection: 208-400 nm.
Starting Compounds and Intermediates:

Example 1A

1-[2-(allyloxy)phenyl]ethanone

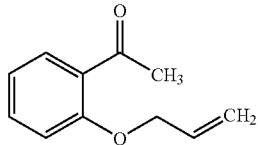

542 g (3.9 mol) of 2-hydroxyacetophenone are heated to reflux with 592 g (4.9 mol) of allyl bromide, 1000 g (7.2 mol) of potassium carbonate and 13.2 g (79 mmol) of potassium iodide in 2.4 liters of acetone for 24 h. Cooling to room temperature is followed by filtration, and the solvent is removed in vacuo. The residue is dissolved in toluene and washed with 10% strength sodium hydroxide solution and water. Concentration results in 689 g (98% of theory) of the title compound.

$^1$H-NMR (300 MHz, CDCl$_3$): δ=2.68 (s, 3H), 4.68 (dd, 2H), 5.89 (dd, 2H), 6.09 (m, 1H), 6.99 (dd, 2H), 7.44 (m, 1H), 7.71 (d, 1H).

Example 2A 1-(3-allyl-2-hydroxyphenyl)ethanone

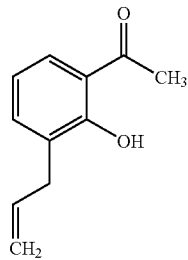

160 g (0.9 mol) of 1-[2-(allyloxy)phenyl]ethanone are stirred in a metal bath at 230-240° C. for 4 h. After cooling to room temperature, the product is distilled in a thin-film evaporator at 140° C. and 0.4 mbar. 155 g (97% of theory) of the title compound are obtained.

$^1$H-NMR (300 MHz, CDCl$_3$): δ=2.68 (s, 3H), 3.44 (d, 2H), 5.09 (m, 2H), 6.01 (m, 1H), 6.85 (t, 1H), 7.38 (dd, 1H), 7.62 (dd, 1H), 12.61 (s, 1H).

Example 3A

1-{2-Hydroxy-3-[(1E)-prop-1-en-1-yl]phenyl}ethanone

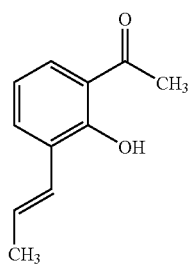

40 g (227 mmol) of 1-(3-allyl-2-hydroxyphenyl)ethanone are dissolved in 120 ml of toluene, and 2.17 g (5.6 mmol) of bis(benzonitrile)dichloropalladium(II) are added. The reaction mixture is heated at 120° C. overnight. Cooling to room temperature is followed by filtration through kieselguhr, and the solvent is removed in vacuo. 20.9 g (95% of theory) of the title compound are obtained and are reacted without further purification in the next stage.

LC-MS (method 1): R$_t$=2.36 min; [M+H]$^+$=177
$^1$H-NMR (300 MHz, CDCl$_3$): δ=1.91 (dd, 3H), 2.63 (s, 3H), 6.32 (m, 1H), 6.73 (dd, 1H), 6.85 (t, 1H), 7.59 (m, 2H), 12.74 (s, 1H).

Example 4A

2-Methyl-8-[(1E)-prop-1-en-1-yl]-4H-chromen-4-one

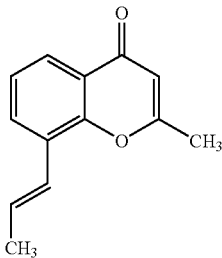

12.52 g (313.2 mmol) of 60% sodium hydride (suspension in mineral oil) are introduced into 300 ml of absolute THF under argon at 10° C. 18.4 g (104.4 mmol) of 1-{2-hydroxy-3-[(1E)-prop-1-en-1-yl]phenyl}ethanone are slowly added dropwise to the suspension. After 15 min, 9 g (114.9 mmol) of acetyl chloride are added. The reaction mixture is stirred at room temperature overnight. Hydrolysis is carried out with 300 ml of water, and the mixture is extracted several times with ethyl acetate. Washing of the organic phase with saturated sodium chloride solution is followed by drying over sodium sulfate. The solvent is then removed in vacuo. The residue is taken up in 200 ml of methanol and heated with 50 ml of 20% strength hydrochloric acid at 80° C. for 30 min. The solvent is then removed in vacuo, and the residue is mixed with 400 ml of water. Several extractions with dichloromethane are carried out. After the organic phase has been dried over magnesium sulfate, the solvent is removed in vacuo and the residue is purified by column chromatography (mobile phase: dichloromethane/methanol 98:2). 10.5 g (50.2% of theory) of the title compound are obtained as a yellow oil.

LC-MS (method 2): R$_t$=2.07 min; [M+H]$^+$=201
$^1$H-NMR (300 MHz, CDCl$_3$): δ=1.98 (dd, 3H), 2.43 (s, 3H), 6.18 (s, 1H), 6.40 (m, 1H), 6.85 (dd, 1H), 7.31 (t, 1H), 7.72 (dd, 1H), 8.05 (dd, 1H).

Example 5A

2-Methyl-4-oxo-4H-chromene-8-carbaldehyde

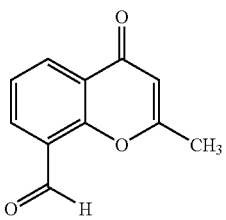

18.5 g (62.8 mmol) of 2-methyl-8-[(1E)-prop-1-en-1-yl]-4H-chromen-4-one are dissolved in 400 ml of dichloromethane and cooled to −60° C. Ozone is passed into the reaction solution for 30 min. Dimethyl sulfide is then added to the reaction mixture. After warming to room temperature, the solvent is removed in vacuo and the residue is slurried in a little methanol. The solid remaining after filtration is recrystallized from diethyl ether. 9.1 g (77.4% of theory) of the title compound are obtained.

LC-MS (method 1): $R_t$=1.31 min; $[M+H]^+$=189

$^1$H-NMR (300 MHz, CDCl$_3$): δ=2.48 (s, 3H), 6.27 (s, 1H), 7.51 (m, 1H), 8.21 (dd, 1H), 8.46 (dd, 1H), 10.67 (s, 1H).

Example 6A

3-[(2-Methyl-4-oxo-4H-chromen-8-yl)methylene]pentane-2,4-dione

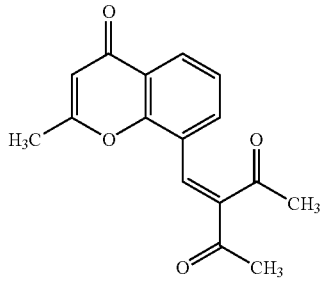 [SMILES: CC(=O)C(=Cc1cccc2c(=O)cc(C)oc12)C(C)=O]

20 g (106 mmol) of 2-methyl-4-oxo-4H-chromene-8-carbaldehyde, 12 ml (116 mmol) of 2,4-pentanedione, 9.1 ml (159 mmol) of acetic acid and 0.21 ml (2.1 mmol) of piperidine in 400 ml of anhydrous dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from isopropanol. 24.3 g (73% of theory) of the title compound are obtained as a white solid.

LC-MS (method 4): $R_t$=1.91 min; $[M+H]^+$=271

$^1$H-NMR (300 MHz, DMSO-d$_6$): δ=2.24 (s, 3H), 2.44 (s, 3H), 2.54 (s, 3H), 6.33 (s, 1H), 7.49 (t, 1H), 7.64 (dd, 1H), 7.97 (s, 1H), 8.07 (dd, 1H).

Example 7A

Ethyl 2-[(2-methyl-4-oxo-4H-chromen-8-yl)methylene]-3-oxobutanoate

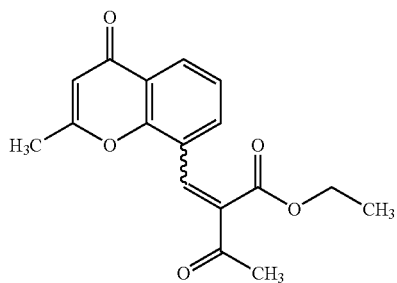 [SMILES: CCOC(=O)C(=Cc1cccc2c(=O)cc(C)oc12)C(C)=O]

5 g (26.57 mmol) of 2-methyl-4-oxo-4H-chromene-8-carbaldehyde, 3.4 ml (26.57 mmol) of ethyl 3-oxobutanoate, 1.9 ml (33.21 mmol) of acetic acid and 263 μl (2.66 mmol) of piperidine in 50 ml of anhydrous dichloromethane are stirred under reflux with a water trap for 24 h. After cooling, the solution is diluted with dichloromethane (50 ml) and washed successively with saturated sodium bicarbonate solution and saturated sodium chloride solution. The organic phase is dried over magnesium sulfate and concentrated. The residue is recrystallized from isopropanol. 7.63 g (91% of theory) of the title compound are obtained as an E/Z mixture.

LC-MS (method 3): $R_t$=1.91 and 2.03 min; $[M+H]^+$=301

$^1$H-NMR (300 MHz, DMSO-d$_6$): δ=1.04 (t, 1.5H), 1.28 (t, 1.5H), 2.34 (s, 1.5H), 2.42 (s, 1.5H), 2.49 (s, 1.5H), 2.55 (s, 1.5H), 4.14 (q, 1H), 4.29 (q, 1H), 6.32 (s, 0.5H), 6.33 (s, 0.5H), 7.47 (t, 0.5H), 7.52 (t, 0.5H), 7.65 (dd, 0.5H), 7.65 (dd, 0.5H), 7.98 (s, 0.5H), 8.07 (dd, 0.5H), 8.08 (s, 0.5H), 8.09 (dd, 0.5H).

Example 8A

4-Bromo-2-(trifluoromethoxy)benzaldehyde

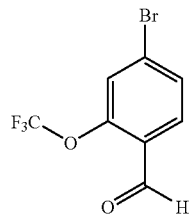 [SMILES: O=Cc1ccc(Br)cc1OC(F)(F)F]

20.00 g (54.51 mmol) of 4-bromo-2-(trifluoromethoxy)iodobenzene are dissolved in 200 ml of THF and cooled to −78° C. Then 26.16 ml (65.41 mmol) of a 2.5 M solution of n-butyllithium in hexane are added dropwise. The mixture is stirred for 30 min and then 14.43 g (125.37 mmol) of N-formylmorpholine are metered in. After complete conversion is detected (TLC check), solvolysis is carried out at −78° C. with isopropanol. Warming to room temperature is followed by addition of water and extraction twice with dichloromethane. The combined organic phases are washed with saturated sodium chloride solution and dried with sodium sulfate, and the solvent is distilled out under reduced pressure. The residue is purified by column chromatography (silica gel, mobile phase:cyclohexane/ethyl acetate 5:1). 11.43 g (78% of theory) of the title compound are obtained.

GC-MS (method 7): $R_t$=4.24 min; MS (EIpos): m/z=270 $[M+H]^+$ $^1$H-NMR (300 MHz, DMSO-d$_6$): δ=7.85-7.92 (m, 3H), 10.20 (s, 1H).

Example 9A

4-Formyl-3-(trifluoromethoxy)benzonitrile

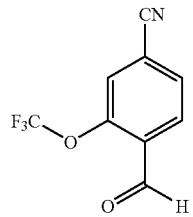 [SMILES: N#Cc1ccc(C=O)c(OC(F)(F)F)c1]

10.63 g (39.51 mmol) of 4-bromo-2-(trifluoromethoxy)benzaldehyde, 3.43 g (29.24 mmol) of zinc cyanide and 1.37 g (1.19 mmol) of tetrakis(triphenylphosphine)palladium(0) are dissolved in 80 ml of DMF. The reaction mixture is then reacted in several portions in a single mode microwave (Emrys Optimizer, 5 min at 220° C.). The combined mixtures are mixed with water and extracted twice with toluene. The combined organic phases are washed with saturated sodium chloride solution and dried with sodium sulfate, and then the solvent is removed in a rotary evaporator. The residue is purified by column chromatography (silica gel, mobile phase: cyclohexane/ethyl acetate 10:1). 3.32 g (78% of theory) of the title compound are obtained with a purity of 80% (according to LC-MS).

MS (EIpos): m/z=215 [M]$^+$ $^1$H-NMR (300 MHz, DMSO-d$_6$): δ=7.85-7.91 (m, 3H), 10.20 (s, 1H).

Example 10A

Sodium 1-cyanoprop-1-en-2-olate

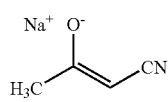

Sodium (7.69 g, 335 mmol) is introduced in portions into 350 ml of anhydrous methanol. After the reaction mixture has been cooled to 25° C., 5-methylisoxazole (27.8 g, 335 mmol) is slowly added in portions (exothermic reaction). After the addition is complete, the mixture is stirred at RT for 4 h and then concentrated. The residue is washed with a little diethyl ether, filtered off with suction and dried under oil pump vacuum. 32.0 g (91 % of theory) of the title compound are obtained.

$^1$H-NMR (400 MHz, DMSO-d$_6$): δ=3.18 (s, 1H), 1.51 (s, 3H).

Example 11A

4-Cyano-2-methoxyphenyl trifluoromethanesulfonate

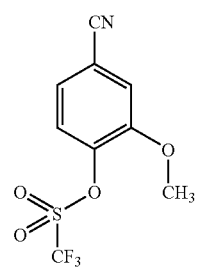 [SMILES: COc1cc(C#N)ccc1OS(=O)(=O)C(F)(F)F]

24 ml (141 mmol) of trifluoromethanesulfonic anhydride are slowly added dropwise to a solution of 20 g (134 mmol) of 4-hydroxy-3-methoxybenzonitrile in pyridine (80 ml), keeping the reaction temperature below 25° C. with the aid of an ice bath. The suspension is then stirred at RT for 1 h. Ice-water (400 ml) is added, and the suspension is stirred further until room temperature is reached. It is then filtered, the solid is dissolved in ethyl acetate, and this solution is washed with saturated sodium chloride solution. The organic phase is dried over magnesium sulfate and concentrated. 37.13 g (92% of theory) of the title compound are obtained as a white solid.

LC-MS (method 4): R$_t$=2.54 min; MS (EIpos): m/z=282 [M+H]$^+$ $^1$H-NMR (300 MHz, DMSO-d$_6$): δ=3.97 (s, 3H), 7.60 (dd, 1H), 7.71 (d, 1H), 7.92 (d, 1H).

Example 12A tert-Butyl (2E)-3-(4-cyano-2-methoxyphenyl)acrylate

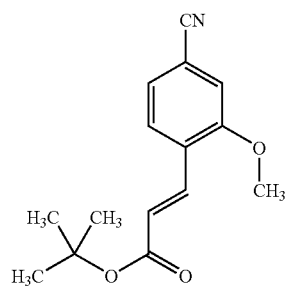 [SMILES: COc1cc(C#N)ccc1/C=C/C(=O)OC(C)(C)C]

4 g (5.7 mmol) of bis(triphenylphosphine)palladium(II) chloride are added to a degassed solution of 37.13 g (132 mmol) of 4-cyano-2-methoxyphenyl trifluoromethanesulfonate, 35 ml (245 mmol) of tert-butyl acrylate and 90 ml (645 mmol) of triethylamine in DMF (250 ml). The solution is stirred at 100° C. under a protective gas atmosphere for 24 h. Ice-water (1000 ml) is then added, and the suspension is extracted with ethyl acetate (3×100 ml). The organic phase is washed with saturated sodium chloride solution, dried over magnesium sulfate and concentrated. The residue is purified by column chromatography (silica gel, mobile phase:cyclohexane/ethyl acetate 10:1). 24.6 g (72% of theory) of the title compound are obtained as a white solid.

LC-MS (method 1): R$_t$=2.59 min; MS (EIpos): m/z=260 [M+H]$^+$ $^1$H-NMR (300 MHz, DMSO-d$_6$): δ=1.48 (s, 9H), 3.93 (s, 3H), 6.65 (d, 1H), 7.42 (d, 1H), 7.58 (s, 1H), 7.74 (d, 1H), 7.89 (d, 1H).

Example 13A

4-Formyl-3-methoxybenzonitrile

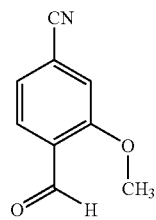

79 g (370 mmol) of sodium metaperiodate are added in portions to a vigorously stirred solution of 48 g (185 mmol) of tert-butyl (2E)-3-(4-cyano-2-methoxyphenyl)acrylate, 207 mg (0.81 mmol) of osmium tetroxide and 1.4 g (6.14 mmol) of benzyltriethylammonium chloride in 750 ml of water/THF (2:1), keeping the reaction temperature below 30° C. The solution is stirred at RT for a further 1 h. Water (2000 ml) is added and the mixture is then filtered. The remaining solid is dissolved in ethyl acetate, and the solution is washed with saturated sodium chloride solution. The organic phase is dried over magnesium sulfate and concentrated. The residue is stirred with petroleum ether. 21.18 g (71% of theory) of the title compound are obtained as a white solid.

LC-MS (method 4): $R_t$=1.87 min; MS (EIpos): m/z=162 [M+H]$^+$ $^1$H-NMR (300 MHz, DMSO-d$_6$): δ=3.98 (s, 3H), 7.53 (d, 1H), 7.80 (s, 1H), 7.81 (d, 1H), 10.37 (s, 1H).

Example 14A 4-(2-Acetyl-3-oxobut-1-en-1-yl)-3-methoxybenzonitrile

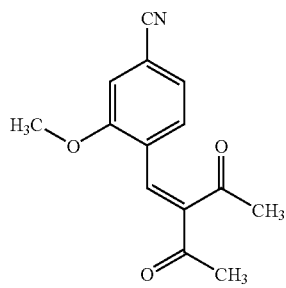 [SMILES: COc1cc(C#N)ccc1C=C(C(C)=O)C(C)=O]

21 g (130 mmol) of 4-formyl-3-methoxybenzonitrile, 14.7 ml (143 mmol) of 2,4-pentanedione, 11.2 ml (195 mmol) of acetic acid and 2.6 ml (26 mmol) of piperidine in 400 ml of dry dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from diethyl ether. 23.2 g (92% of theory) of the title compound are obtained as a pale brown solid.

LC-MS (method 4): $R_t$=2.05 min; [M+H]$^+$=244

$^1$H-NMR (300 MHz, DMSO-d$_6$): δ=2.20 (s, 3H), 2.42 (s, 3H), 3.89 (s, 3H), 7.37 (d, 1H), 7.46 (dd, 1H), 7.60 (d, 1H), 7.68 (s, 1H).

Example 15A 4-(2-Acetyl-3-oxobut-1-en-1-yl)benzonitrile

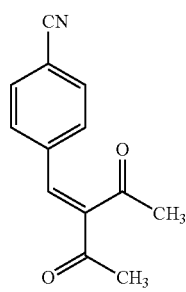 [SMILES: CC(=O)C(=Cc1ccc(C#N)cc1)C(C)=O]

2.3 g (17.5 mmol) of 4-formylbenzonitrile, 1.98 ml (19.29 mmol) of 2,4-pentanedione, 1 ml (26 mmol) of acetic acid and 0.34 ml (3.5 mmol) of piperidine in 40 ml of anhydrous dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from diethyl ether. 3.18 g (85% of theory) of the title compound are obtained as a pale brown solid.

$^1$H-NMR (300 MHz, DMSO-d$_6$): δ=2.26 (s, 3H), 2.46 (s, 3H), 7.60 (d, 2H), 7.76 (s, 1H), 7.93 (d, 2H).

Example 16A

9-Oxo-9H-fluorene-4-carbaldehyde

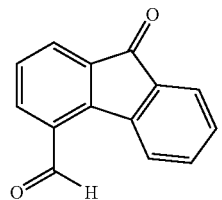 [SMILES: O=Cc1cccc2c1-c1ccccc1C2=O]

Methyl 9-oxo-9H-fluorene-4-carboxylate (9.85 g, 41.3 mmol) is introduced under argon into 180 ml of anhydrous THF. At RT, RED-AL® (38 ml, 136 mmol) [sodium bis-(2-methoxyethoxy)aluminum dihydride, 70% strength solution in toluene] is added dropwise over the course of 90 min, and the reaction mixture is then stirred for 1 h. The mixture is hydrolyzed by cautious dropwise addition of 15 ml of water. 60 ml of 6N hydrochloric acid are then added, and the mixture is extracted with ethyl acetate (4×150 ml each time). The combined organic phases are washed with saturated sodium chloride solution (2×100 ml each time), dried over sodium sulfate and concentrated in a rotary evaporator. 12.1 g of the corresponding alcohol are obtained. 8.77 g (41.3 mmol) of this are dissolved in 200 ml of dioxane, and activated manganese dioxide (25.1 g, 289 mmol) is added. The mixture is stirred at RT for 1 h and then at 50° C. for 30 min. The oxidizing agent is filtered off with suction, the residue on the filter is washed with dioxane (3×50 ml each time), and the filtrate is concentrated in a rotary evaporator. The resulting crude material is purified by chromatography on silica gel (mobile phase gradient:cyclohexane cyclohexane/ethyl acetate 3:1). 6.50 g (76% of theory) of the title compound are obtained.

LC-MS (method 5): $R_t$=2.14 min; MS (ESIpos): m/z=209 [M+H]$^+$ $^1$H-NMR (400 MHz, DMSO-d$_6$): δ=7.50 (dd, 1H), 7.62 (dd, 1H), 7.69 (m, 2H), 7.90 (d, 1H), 8.12 (d, 1H), 8.39 (d, 1H), 10.5 (s, 1H).

Example 17A

3-Oxo-2-[(9-oxo-9H-fluoren-4-yl)methylene]butanenitrile

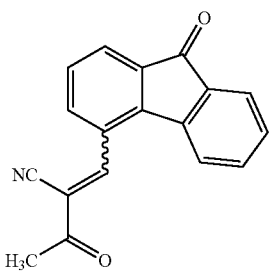

The compound from example 11A (5.21 g, 25.0 mmol) is introduced into 180 ml of dichloromethane, and the compound from example 16A (2.89 g, 27.5 mmol), acetic acid (1.72 ml, 30.0 mmol) and piperidine (0.25 ml, 2.50 mmol) are added. The mixture is stirred at the boiling point with a water trap for 4 h. Cooling to RT is followed by dilution with 30 ml of dichloromethane and washing with water (2×50 ml), the organic phase is dried over sodium sulfate and the solvent is removed in a rotary evaporator. The resulting crude product is purified by chromatography on silica gel 60 with dichloromethane as mobile phase. Combining the product fractions and removing the solvent results in 5.40 g (79% of theory) of the title compound as mixture of E/Z isomers.

LC-MS (method 5): $R_t$=2.24 min; MS (ESIpos): m/z=274 [M+H]$^+$ $^1$H-NMR (400 MHz, DMSO-d$_6$): δ=2.64 (s, 3H), 7.49 (t, 1H), 7.59 (t, 1H), 7.64 (d, 1H), 7.69 (d, 1H), 7.73 (d, 1H), 7.81 (d, 1H), 7.90 (d, 1H), 8.88 (s, 1H).

Example 18A

6-Ethoxypyrimidine-2,4-diamine

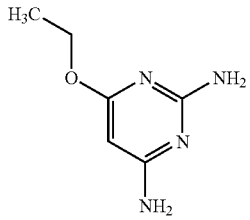

174 mg of sodium hydride (60% in mineral oil, 4.36 mmol) are added in portions under an argon atmosphere to a vigorously stirred solution of 500 mg (3.96 mmol) of 2,6-diaminopyrimidin-4-ol in 10 ml of DMF. After 30 min, 700 μl (5.15 mmol) of ethyl trifluoromethanesulfonate are added dropwise, and the solution is stirred for a further 20 min. Methanol (1 ml) is then added to the reaction mixture, which is directly purified by preparative HPLC. Combining the product fractions and removing the solvent result in 370 mg (64% of theory) of the title compound as a white solid.

LC-MS (method 5): $R_t$=2.24 min; MS (ESIpos): m/z=155 [M+H]$^+$ $^1$H-NMR (400 MHz, DMSO-d$_6$): δ=1.21 (t, 3H), 4.12 (q, 2H), 5.00 (s, 1H), 5.87 (s, 2H), 6.01 (s, 2H).

Example 19A

6-Acetyl-7-methyl-5-(2-methyl-4-oxo-4H-chromen-8-yl)-5,8-dihydropyrido[2,3-d]pyrimidin-4(3H)-one

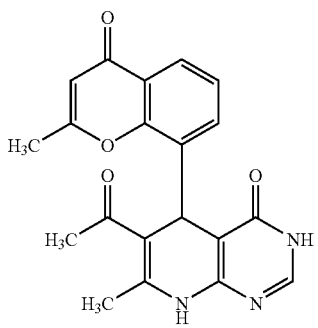 [SMILES: CC(=O)C1=C(C)Nc2nc[nH]c(=O)c2C1c1cccc2c(=O)cc(C)oc12]

500 mg (1.85 mmol) of 3-[(2-methyl-4-oxo-4H-chromen-8-yl)methylene]pentane-2,4-dione are mixed with 308 mg (2.77 mmol) of 6-aminopyrimidin-4(3H)-one, dissolved in 10 ml of isopropanol and heated under reflux under argon for 2 days. The mixture is then concentrated and the residue is recrystallized from methanol. 341 mg (51% of theory) of the title compound are obtained as a yellow solid.

LC-MS (method 1): $R_t$=1.08 min; [M+H]$^+$=364

$^1$H-NMR (300 MHz, DMSO-d): δ=2.12 (s, 3H), 2.30 (s, 3H), 2.36 (s, 3H), 5.49 (s, 1H), 6.18 (s, 1H), 7.33 (t, 1H), 7.66 (dd, 1H), 7.80 (dd, 1H), 7.91 (s, 1H), 9.35 (s, 1H), 11.95 (br.s, 1H).

Example 20A

6-Isopropoxypyrimidine-2,4-diamine

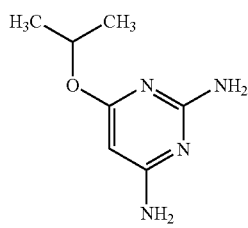

634 mg of sodium hydride (60% in mineral oil, 17.12 mmol) are added in portions under an argon atmosphere to a vigorously stirred solution of 1.8 g (14.27 mmol) of 2,6-diaminopyrimidin-4-ol in 20 ml of DMF. After 30 min, 1.6 ml (17.12 mmol) of isopropyl bromide are added dropwise, and the solution is stirred at 40° C. for 12 h. Methanol (1 mol) is then added to the reaction mixture, which is directly purified by preparative HPLC. Combining the product fractions and removing the solvent result in 250 mg (12% of theory) of the title compound as a white solid.

LC-MS (method 5): $R_t$=2.31 min; MS (ESIpos): m/z=169 [M+H]$^+$ $^1$H-NMR (400 MHz, DMSO-d$_6$): δ=1.31 (d, 6H), 5.22 (s, 1H), 5.25 (m, 1H), 6.19 (s, 2H), 7.25 (s, 2H).

Example 21A 8-(6-Acetyl-2-amino-4-hydroxy-7-methyl-5,8-dihydropyrido[2,3-d]pyrimidin-5-yl)-2-methyl-4H-chromen-4-one

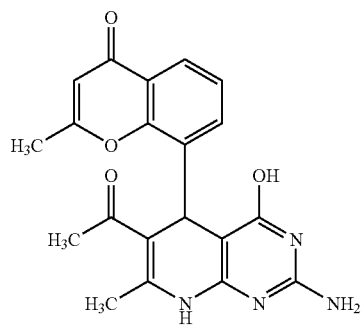 [SMILES: CC(=O)C1=C(C)Nc2nc(N)nc(O)c2C1c1cccc2c(=O)cc(C)oc12]

500 mg (1.85 mmol) of 3-[(2-methyl-4-oxo-4H-chromen-8-yl)methylene]pentane-2,4-dione are mixed with 349 mg (2.77 mmol) of 2,6-diaminopyrimidin-4-ol, dissolved in 10 ml of isopropanol, and heated under reflux under argon for 2 days. The mixture is filtered and the remaining solid is washed with isopropanol. 660 mg (94% of theory) of the title compound are obtained as a white solid.

LC-MS (method 1): $R_t$=1.03 min; $[M+H]^+$=379

$^1$H-NMR (300 MHz, DMSO-d$_6$): δ=2.08 (s, 3H), 2.27 (s, 3H), 2.36 (s, 3H), 5.34 (s, 1H), 6.17 (s, 1H), 6.28 (s, 2H), 7.30 (t, 1H), 7.62 (dd, 1H), 7.78 (dd, 1H), 9.25 (s, 1H), 10.22 (s, 1H).

Example 22A

Ethyl 2-(4-cyano-2-methoxybenzylidene)-3-oxobutanoate

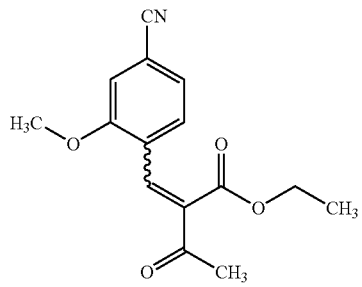 [SMILES: CCOC(=O)C(=Cc1ccc(C#N)cc1OC)C(C)=O]

3 g (18.61 mmol) of 4-formyl-3-methoxybenzonitrile, 2.6 ml (20.47 mmol) of ethyl 3-oxobutanoate, 1.33 ml (23.26 mmol) of acetic acid and 0.18 ml (1.85 mmol) of piperidine are stirred in 70 ml of dry dichloromethane under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from diethyl ether. 5.01 g (98% of theory) of the title compound are obtained as E/Z isomer mixture in the form of a pale yellow solid.

$^1$H-NMR (300 MHz, DMSO-d$_6$): δ=1.11 (t, 2H), 1.26 (t, 1H), 2.31 (s, 1H), 2.42 (s, 2H), 3.88 (s, 1H), 3.90 (s, 2H), 4.16 (q, 1.3H), 4.25 (q, 0.7H), 7.38 (d, 0.35H), 7.42 (d, 0.75H), 7.45 (dd, 0.35H), 7.49 (dd, 0.65H), 7.60 (d, 0.35H), 7.62 (d, 0.65H), 7.67 (s, 0.35H), 7.80 (s, 0.65H).

Example 23A

Ethyl 2-(4-cyano-2-methoxybenzylidene)-4,4-diethoxy-3-oxobutanoate

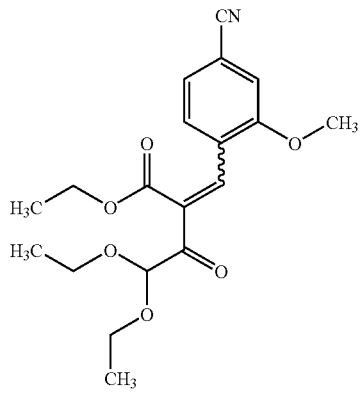 [SMILES: CCOC(=O)C(=Cc1ccc(C#N)cc1OC)C(=O)C(OCC)OCC]

618.2 mg (2.83 mmol) of ethyl 4,4-diethoxy-3-oxobutanoate [Johnson et al., *J. Am. Chem. Soc.* 41, 812 (1919)], 500.0 mg (2.58 mmol) of 4-formyl-3-methoxybenzonitrile, 232.0 mg (3.86 mmol) of acetic acid and 43.9 mg (0.51 mmol) of piperidine are dissolved in 20 ml of dichloromethane and heated under reflux with an inverse water trap overnight. Cooling is followed by washing twice with water, and the organic phase is dried with magnesium sulfate. The solvent is removed in a rotary evaporator, and the residue is purified by column chromatography (silica gel, mobile phase:cyclohexane/ethyl acetate 4:1). 824 mg (77.0% of theory) of the title compound are obtained as a mixture of the E/Z isomers.

LC-MS (method 4): $R_t$=2.63 min and 2.69 min; $[M-EtOH+H]^+$ (EIpos): m/z=316.

Example 24A

Ethyl 5-acetyl-4-(4-cyano-2-methoxyphenyl)-2-formyl-6-methyl-1,4-dihydropyridine-3-carboxylate

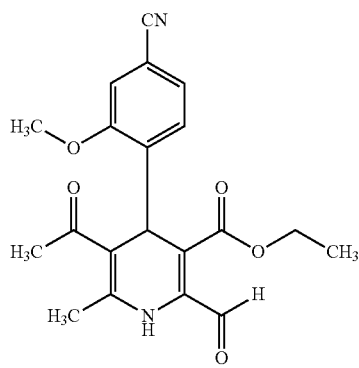 [SMILES: CCOC(=O)C1=C(C=O)NC(C)=C(C(C)=O)C1c1ccc(C#N)cc1OC]

720 mg (1.992 mmol) of ethyl 2-(4-cyano-2-methoxybenzylidene)-4,4-diethoxy-3-oxobutanoate are taken up in 15 ml of isopropanol, 197.5 mg (4.84 mmol) of 4-amino-3-penten-2-one are added, and the mixture is heated at the reflux temperature overnight. The mixture is then concentrated and the residue is purified by preparative HPLC (eluent: acetonitrile/water with 0.1% formic acid, gradient 20:80→95:5). 250 mg (28.6% of theory) of ethyl 5-acetyl-4-(4-cyano-2-methoxyphenyl)-2-(diethoxymethyl)-6-methyl-1,4-dihydropyridine-3-carboxylate are obtained [LC-MS (method 11): $R_t$=2.48 min; $[M+H]^+$ (EIpos): m/z=443].

250 mg (0.565 mmol) of the dihydropyridine acetal obtained in this way are taken up in 7 ml of acetone, and 0.38 ml of 6N hydrochloric acid is added. The mixture is stirred at room temperature until complete conversion is detected (about 2 h, TLC check). The reaction mixture is neutralized with sodium bicarbonate solution, and the acetone is removed in a rotary evaporator. Extraction is carried out three times with ethyl acetate, and the combined organic phases are washed with sodium bicarbonate solution. After drying with magnesium sulfate, the solvent is distilled out under reduced pressure, and the residue is dried under high vacuum. 824 mg (77.0% of theory) of the title compound are obtained.

LC-MS (method 1): $R_t$=2.00 min; [M+H]$^+$ (EIpos): m/z=369

$^1$H-NMR (300 MHz, DMSO-d$_6$): δ=1.21 (t, 3H), 2.18 (s, 3H), 2.33 (s, 3H), 3.82 (s, 3H), 4.17 (m, 2H), 5.37 (s, 1H), 7.12 (d, 1H), 7.33 (d, 1H), 7.43 (s, 1H), 9.06 (s, 1H), 10.90 (br. s, 1H).

Example 25A 4-(3-Acetyl-2-methyl-5-oxo-1,4,5,6-tetrahydropyrido[2,3-d]pyridazin-4-yl)-3-methoxybenzonitrile

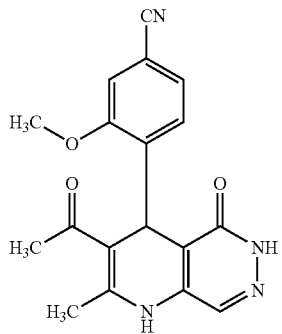 [SMILES: COc1cc(C#N)ccc1C1C(C(C)=O)=C(C)Nc2cn[nH]c(=O)c21]

208 mg (0.565 mmol) of ethyl 5-acetyl-4-(4-cyano-2-methoxyphenyl)-2-formyl-6-methyl-1,4-dihydropyridine-3-carboxylate and 41.5 mg (0.830 mmol) of hydrazine hydrate are taken up in 6.6 ml of ethanol/acetic acid (10:1) and reacted at 100° C. for 5 h. The volatile components are removed in a rotary evaporator, and the residue is taken up in acetonitrile. The precipitated product is filtered off and dried under high vacuum. 66 mg (34.7% of theory) of the title compound are obtained.

LC-MS (method 4): $R_t$=1.49 min; [M+H]$^+$ (EIpos): m/z=337

$^1$H-NMR (300 MHz, DMSO-d$_6$): δ=2.14 (s, 3H), 2.19 (s, 3H), 3.81 (s, 3H), 5.36 (s, 1H), 7.20 (d, 1H), 7.31 (dd, 1H), 7.42 (d, 1H), 7.64 (s, 1H), 9.51 (s, 1H), 12.47 (s, 1H).

Example 26A

Ethyl 4-(4-cyano-2-methoxyphenyl)-2-methyl-5-oxo-1,4,5,6-tetrahydropyrido[2,3-d]pyridazine-3-carboxylate

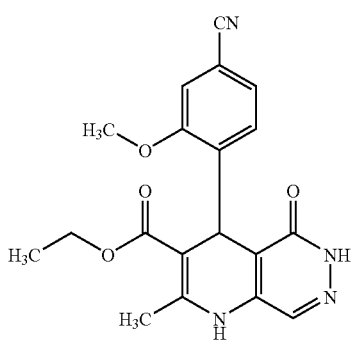 [SMILES: CCOC(=O)C1=C(C)Nc2cn[nH]c(=O)c2C1c1ccc(C#N)cc1OC]

Diethyl 4-(4-cyano-2-methoxyphenyl)-2-formyl-6-methyl-1,4-dihydropyridine-3,5-dicarboxylate can be obtained in analogy to the preparation of example 24A from ethyl 3-aminobut-2-enoate and ethyl 2-(4-cyano-2-methoxybenzylidene)-4,4-diethoxy-3-oxobutanoate (example 23A) [cf. also Satoh et al., *Chem. Pharm. Bull.* 39, 3189-3201 (1991)].

115.5 mg (0.290 mmol) of the formyl dihydropyridine prepared in this way and 21.3 mg (0.426 mmol) of hydrazine hydrate are taken up in 6.6 ml of ethanol/acetic acid (10:1) and reacted at 100° C. for 5 h. The volatile components are removed in a rotary evaporator, and the residue is purified by column chromatography (Biotage 40S cartridge, eluent: ethyl acetate). The product fractions are concentrated, the residue is stirred with dichoromethane, the precipitated product is filtered off, and the yellow crystals are dried under high vacuum. 67 mg (63.0% of theory) of the title compound are obtained.

LC-MS (method 1): $R_t$=1.57 min; [M+H]$^+$ (EIpos): m/z=367

$^1$H-NMR (300 MHz, DMSO-d$_6$): δ=1.09 (t, 3H), 2.27 (s, 3H), 3.76 (s, 3H), 3.92 (m, 2H), 5.23 (s, 1H), 7.29 (s, 2H), 7.37 (s, 1H), 7.59 (s, 1H), 9.51 (s, 1H), 12.40 (s, 1H).

Exemplary Embodiments:

Example 1

8-(6-Acetyl-4-ethoxy-7-methyl-5,8-dihydropyrido[2,3-d]pyrimidin-5-yl)-2-methyl-4H-chromen-4-one

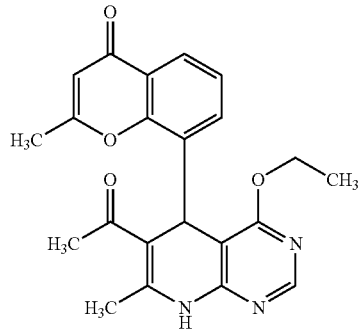 [SMILES: CCOc1ncnc2c1C(c1cccc3c(=O)cc(C)oc13)C(C(C)=O)=C(C)N2]

140 mg (0.38 mmol) of 6-acetyl-7-methyl-5-(2-methyl-4-oxo-4H-chromen-8-yl)-5,8-dihydropyrido[2,3-d]pyrimidin-4(3H)-one are suspended under an argon atmosphere in dichloromethane (7 ml), 219 mg (1.15 mmol) of triethyloxonium tetrafluoroborate are added, and the mixture is stirred at RT for 12 h. The reaction mixture is then mixed with methanol and concentrated. The residue is purified by preparative HPLC to result in 9 mg (6% of theory) of the title compound are obtained as a white solid.

LC-MS (method 1): $R_t$=1.62 min; [M+H]$^+$=392

$^1$H-NMR (300 MHz, DMSO-d$_6$): δ=1.05 (t, 3H), 2.14 (s, 3H), 2.35 (s, 3H), 2.39 (s, 3H), 4.15 (m, 2H), 5.65 (s, 1H), 6.22 (s, 1H), 7.34 (t, 1H), 7.66 (dd, 1H), 7.82 (dd, 1H), 8.25 (s, 1H), 10.06 (s, 1H).

Example 2

6-Acetyl-2-amino-7-methyl-5-(2-methyl-4-oxo-4H-chromen-8-yl)-5,8-dihydropyrido [2,3-d]-pyrimidin-4-yl trifluoromethanesulfonate

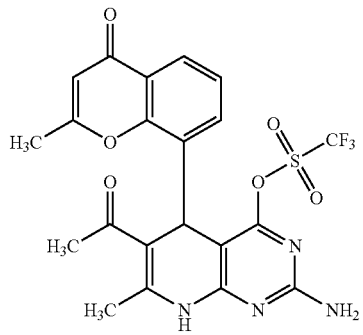 [SMILES: CC(=O)C1=C(C)Nc2nc(N)nc(OS(=O)(=O)C(F)(F)F)c2C1c1cccc2c(=O)cc(C)oc12]

200 mg (0.52 mmol) of 8-(6-acetyl-2-amino-4-hydroxy-7-methyl-5,8-dihydropyrido[2,3-d]-pyrimidin-5-yl)-2-methyl-4H-chromen-4-one are introduced into 5 ml of pyridine, 188 μl (1.057 mmol) of trifluoromethanesulfonic anhydride are added, and the mixture is stirred at RT for 30 min. The mixture is then concentrated and the residue is purified by preparative HPLC (eluent:acetonitrile/water with 0.1% formic acid, gradient 20:80→95:5). 95 mg (35% of theory) of the title compound are obtained as a pale yellow solid.

LC-MS (method 1): $R_t$=1.85 min; MS (EIpos): m/z=510 [M+H]$^+$ $^1$H-NMR (300 MHz, DMSO-d$_6$): δ=2.16 (s, 3H), 2.32 (s, 3H), 2.34 (s, 3H), 5.52 (s, 1H), 6.20 (s, 1H), 6.95 (s, 2H), 7.36 (t, 1H), 7.60 (dd, 1H), 7.84 (dd, 1H), 10.18 (s, 1H).

Example 3

6-Acetyl-7-methyl-5-(2-methyl-4-oxo-4H-chromen-8-yl)-5,8-dihydropyrido[2,3-d]pyrimidin-4-yl trifluoromethanesulfonate

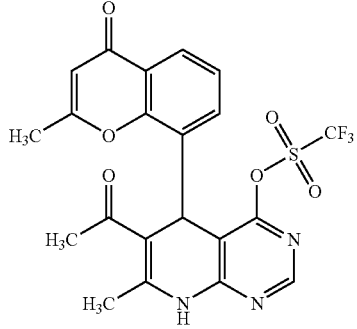 [SMILES: CC(=O)C1=C(C)Nc2ncnc(OS(=O)(=O)C(F)(F)F)c2C1c1cccc2c(=O)cc(C)oc12]

50 mg (0.13 mmol) of 6-acetyl-7-methyl-5-(2-methyl-4-oxo-4H-chromen-8-yl)-5,8-dihydropyrido-[2,3-d]pyrimidin-4(3H)-one are introduced into 2 ml of pyridine, 29 μl (0.165 mmol) of trifluoromethanesulfonic anhydride are added, and the mixture is stirred at RT for 30 min. The mixture is then concentrated and the residue is purified by preparative HPLC (eluent:acetonitrile/water with 0.1% formic acid, gradient 20:80→95:5). 31 mg (45% of theory) of the title compound are obtained as a pale yellow solid.

LC-MS (method 2): $R_t$=2.31 min; MS (EIpos): m/z=496 [M+H]$^+$ $^1$H-NMR (300 MHz, DMSO-d$_6$): δ=2.21 (s, 3H), 2.33 (s, 3H), 2.36 (s, 3H), 5.79 (s, 1H), 6.21 (s, 1H), 7.38 (t, 1H), 7.68 (dd, 1H), 7.88 (dd, 1H), 8.52 (s, 1H), 10.79 (s, 1H).

Example 4

8-(6-Acetyl-2-amino-4-ethoxy-7-methyl-5,8-dihydropyrido[2,3-d]pyrimidin-5-yl)-2-methyl-4H-chromen-4-one

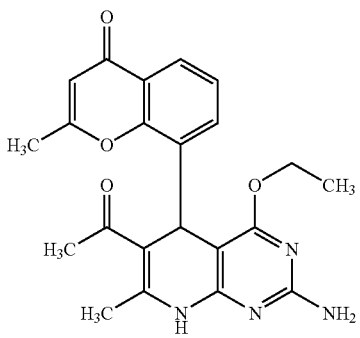 [SMILES: CCOc1nc(N)nc2c1C(c1cccc3c(=O)cc(C)oc13)C(C(C)=O)=C(C)N2]

270 mg (1 mmol) of 3-[(2-methyl-4-oxo-4H-chromen-8-yl)methylene]pentane-2,4-dione and 170 mg (1.1 mmol) of 6-ethoxypyrimidine-2,4-diamine are dissolved in 5 ml of isopropanol and heated under reflux under argon for 2 days. The mixture is then concentrated and the residue is purified by preparative HPLC. 230 mg (56% of theory) of the title compound are obtained as a yellow solid.

LC-MS (method 3): $R_t$=1.68 min; [M+H]$^+$=407

$^1$H-NMR (400 MHz, DMSO-d$_6$): δ=1.00 (t, 3H), 2.09 (s, 3H), 2.31 (s, 3H), 2.39 (s, 3H), 4.04 (m, 2H), 5.48 (s, 1H), 6.18 (s, 2H), 6.21 (s, 1H), 7.32 (t, 1H), 7.59 (dd, 1H), 7.79 (dd, 1H), 9.49 (s, 1H).

Example 5

8-(6-Acetyl-2-amino-4-isopropoxy-7-methyl-5,8-dihydropyrido[2,3-d]pyrimidin-5-yl)-2-methyl-4H-chromen-4-one

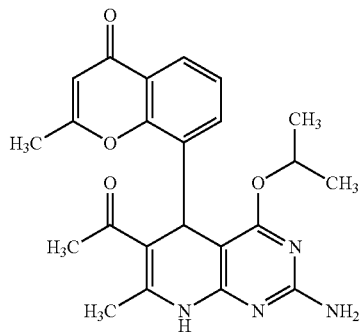 [SMILES: CC(=O)C1=C(C)Nc2nc(N)nc(OC(C)C)c2C1c1cccc2c(=O)cc(C)oc12]

100 mg (0.37 mmol) of 3-[(2-methyl-4-oxo-4H-chromen-8-yl)methylene]pentane-2,4-dione and 62 mg (0.37 mmol) of 6-isopropoxypyrimidine-2,4-diamine are dissolved in 5 ml of isopropanol and heated under reflux under argon for 2 days. The mixture is filtered and the remaining solid is washed with isopropanol. 80 mg (51% of theory) of the title compound are obtained as a white solid.

LC-MS (method 1): $R_t$=1.63 min; [M+H]$^+$=421

$^1$H-NMR (400 MHz, DMSO-d$_6$): δ=0.66 (t, 3H), 1.19 (t, 3H), 2.08 (s, 3H), 2.30 (s, 3H), 2.40 (s, 3H), 5.01 (m, 1H), 5.44 (s, 1H), 6.15 (s, 2H), 6.22 (s, 1H), 7.32 (t, 1H), 7.58 (dd, 1H), 7.78 (dd, 1H), 9.46 (s, 1H).

Example 6

2-Amino-4-isopropoxy-7-methyl-5-(9-oxo-9H-fluoren-4-yl)-5,8-dihydropyrido[2,3-d]pyrimidine-6-carbonitrile

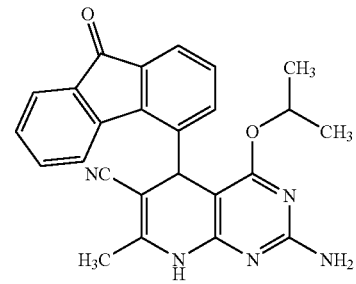

81 mg (0.29 mmol) of 3-oxo-2-[(9-oxo-9H-fluoren-4-yl)methylene]butanenitrile are dissolved with 50 mg (0.29 mmol) of 6-isopropoxypyrimidine-2,4-diamine in 5 ml of isopropanol and heated under reflux under argon for 6 h. The suspension is cooled and then filtered with suction, and the remaining solid is washed with isopropanol. 74 mg (59% of theory) of the title compound are obtained as a white solid.

LC-MS (method 8): $R_t$=4.29 min; $[M+H]^+$=424

$^1$H-NMR (400 MHz, CDCl$_3$): δ=0.53 (d, 3H), 0.92 (d, 3H), 2.22 (s, 3H), 4.68 (s, 2H), 5.01 (m, 1H), 5.57 (s, 1H), 6.49 (s, 1H), 7.20 (t, 1H), 7.31 (t, 2H), 7.51 (t, 1H), 7.55 (d, 1H), 7.72 (d, 1H), 7.98 (d, 1H).

Example 7

Ethyl 4-amino-5-(4-cyano-2-methoxyphenyl)-7-methyl-2-(methylthio)-5,8-dihydropyrido[2,3-d]-pyrimidine-6-carboxylate

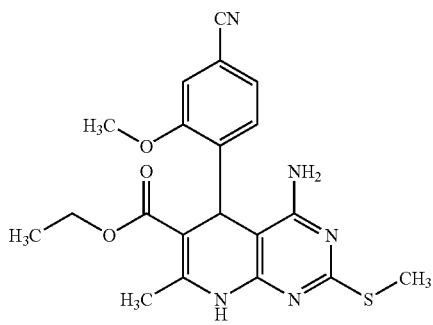 [SMILES: CCOC(=O)C1=C(C)Nc2nc(SC)nc(N)c2C1c1ccc(C#N)cc1OC]

740 mg (2.70 mmol) of ethyl 2-(4-cyano-2-methoxybenzylidene)-3-oxobutanoate and 422 mg (2.70 mmol) of 2-(methylthio)pyrimidine-4,6-diamine are dissolved in 5 ml of isopropanol and heated under reflux under argon for 12 h. The mixture is filtered and the remaining solid is washed with isopropanol. 395 mg (35% of theory) of the title compound are obtained as a white solid.

LC-MS (method 1): $R_t$=2.06 min; $[M+H]^+$=412

$^1$H-NMR (400 MHz, DMSO-d$_6$): δ=1.02 (t, 3H), 2.33 (s, 3H), 2.36 (s, 3H), 3.86 (q, 2H), 3.90 (s, 3H), 5.19 (s, 1H), 6.27 (s, 2H), 7.36 (s, 2H), 7.47 (s, 1H), 7.92 (dd, 1H), 9.58 (s, 1H).

Example 8

4-(3-Acetyl-5-ethoxy-2-methyl-1,4-dihydropyrido[2,3-d]pyridazin-4-yl)-3-methoxybenzonitrile

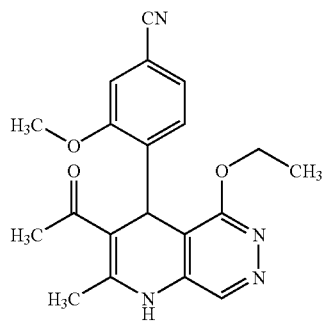 [SMILES: CCOc1nncc2c1C(c1ccc(C#N)cc1OC)C(C(C)=O)=C(C)N2]

65 mg (0.193 mmol) of 4-(3-acetyl-2-methyl-5-oxo-1,4,5,6-tetrahydropyrido[2,3-d]pyridazin-4-yl)-3-methoxybenzonitrile are mixed under an argon atmosphere with 4 ml of abs. dichloromethane and 73.4 mg (0.386 mmol) of triethyloxonium tetrafluoroborate. After a reaction time of 2 hours at room temperature (reaction check by HPLC), conversion remains incomplete. Two further equivalents of triethyloxonium tetrafluoroborate are added. After a further reaction time of 3 h, the mixture is mixed with 5 ml of methanol and 0.5 ml of water and again stirred for 2 h. It is then diluted with 20 ml of water and extracted three times with dichloromethane. The combined organic phases are dried with sodium sulfate, and the solvent is removed in a rotary evaporator. The residue is purified by preparative HPLC (eluent: acetonitrile/water with 0.1% formic acid, gradient 20:80→95:5). 8 mg (11.3% of theory) of the title compound are obtained.

LC-MS (method 1): $R_t$=1.68 min; $[M+H]^+$ (EIpos): m/z=365

$^1$H-NMR (300 MHz, DMSO-d$_6$): δ=1.20 (t, 3H), 2.11 (s, 3H), 2.28 (s, 3H), 3.84 (s, 3H), 4.27 (m, 2H), 5.47 (s, 1H), 7.26 (d, 1H), 7.31 (dd, 1H), 7.41 (d, 1H), 8.48 (s, 1H), 9.66 (s, 1H).

Example 9

Ethyl 4-(4-cyano-2-methoxyphenyl)-5-ethoxy-2-methyl-1,4-dihydropyrido[2,3-d]pyridazine-3-carboxylate

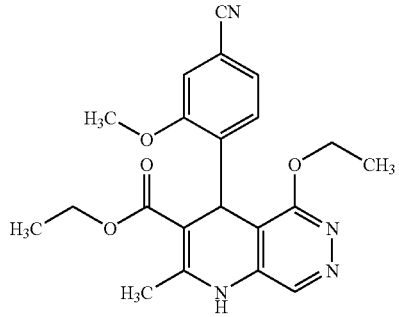 [SMILES: CCOC(=O)C1=C(C)Nc2cnnc(OCC)c2C1c1ccc(C#N)cc1OC]

50 mg (0.136 mmol) of ethyl 4-(4-cyano-2-methoxyphenyl)-2-methyl-5-oxo-1,4,5,6-tetrahydropyrido[2,3-d]pyridazine-3-carboxylate are mixed under an argon atmosphere with 5 ml of abs. dichloromethane and 51.8 mg (0.273 mmol) of triethyloxonium tetrafluoroborate. After a reaction time of 2 hours at room temperature, the mixture is mixed with 5 ml of methanol and 0.5 ml of water and again stirred for 1 h. It is then diluted with 20 ml of water and extracted three times with dichloromethane. The combined organic phases are dried with magnesium sulfate, and the solvent is removed in a rotary evaporator. The residue is purified by preparative HPLC (eluent:acetonitrile/water with 0.1% formic acid, gradient 20:80→95:5). 15 mg (27.8% of theory) of the title compound are obtained.

LC-MS (method 1): $R_t$=1.97 min; $[M+H]^+$ (EIpos): m/z=395

$^1$H-NMR (300 MHz, DMSO-d$_6$): δ=1.06 (t, 3H), 1.17 (t, 3H), 2.33 (s, 3H), 3.79 (s, 3H), 3.90 (q, 2H), 4.24 (m, 2H), 5.36 (s, 1H), 7.29 (m, 2H), 7.36 (s, 1H), 8.45 (s, 1H), 9.66 (s, 1H).

B. Assessment of the Pharmacological Activity

Abbreviations:

| Abbreviations: | |
|---|---|
| DMEM | Dulbecco's modified Eagle medium |
| DNA | deoxyribonucleic acid |
| FCS | fetal calf serum |
| HEPES | 4-(2-hydroxyethyl)-1-piperazineethanesulfonic acid |
| PCR | polymerase chain reaction |
| Tris | tris-(hydroxymethyl)methylamine |

The advantageous pharmacological properties of the compounds of the invention can be shown in the following assays:

1. Cellular in vitro Assay to Determine the Inhibitory MR Activity and MR Selectivity Compared with other Steroid Hormone Receptors Antagonists of the human mineralocorticoid receptor (MR) are identified, and the activity of the compounds described herein is quantified with the aid of a recombinant cell line. The cell is originally derived from a hamster ovary epithelial cell (Chinese Hamster Ovary, CHO K1, ATCC: American Type Culture Collection, VA 20108, USA).

An established chimera system in which the ligand-binding domains of human steroid hormone receptors are fused to the DNA-binding domain of the yeast transcription factor GAL4 is used in this CHO K1 cell line. The GAL4-steroid hormone receptor chimeras produced in this way are cotransfected and stably expressed with a reporter construct in the CHO cells.

Clonings:

To generate the GAL4-steroid hormone receptor chimeras, the GAL4 DNA binding domain (amino acids 1-147) from the vector pFC2-dbd (from Stratagene) is cloned with the PCR-amplified ligand-binding domains of the mineralocorticoid receptor (MR, amino acids 734-985), of the glucocorticoid receptor (GR, amino acids 443-777), of the progesterone receptor (PR, amino acids 680-933) and of the androgen receptor (AR, amino acids 667-919) into the vector pIRES2 (from Clontech). The reporter construct, which comprises five copies of the GAL4 binding site upstream of a thymidine kinase promoter, leads to expression of firefly-luciferase (*Photinus pyralis*) after activation and binding of the GAL4-steroid hormone receptor chimeras by the respective specific agonists aldosterone (MR), dexamethasone (GR), progesterone (PR) and dihydrotestosterone (AR).

Assay Procedure:

The MR, GR, PR and AR cells are plated out in medium (Optimem, 2.5% FCS, 2 mM glutamine, 10 mM HEPES) in 96- (or 384- or 1536-) well microtiter plates on the day before the assay and are kept in a cell incubator (96% humidity, 5% v/v $CO_2$, 37° C.). On the day of the assay, the substances to be tested are taken up in the abovementioned medium and added to the cells. About 10 to 30 minutes after addition of the test substances, the respective specific agonists of the steroid hormone receptors are added. After a further incubation time of 5 to 6 hours, the luciferase activity is measured with the aid of a video camera. The measured relative light units as a function of the substance concentration result in a sigmoidal stimulation curve. The $IC_{50}$ values are calculated with the aid of the GraphPad PRISM computer program (Version 3.02).

In the MR assay, the compounds of the invention have $IC_{50}$ values in the range 20-250 nM.

2. In vitro Assay to Determine Possible Binding Activity to the L-type Calcium Channel Membrane preparations of the cerebral cortex of Wistar rats serve as starting material for a radioactive binding assay which is described in detail in the literature as standard assay [Ehlert, F. J., Roeske, W. R., Itoga E., Yamamura, H. I., *Life Sci*. 30, 2191-2202 (1982); Gould, R. J., Murphy, K. M. M., Snyder, S. H., *Proc. Natl. Acad. Sci. U.S.A*. 79, 3656-3660] and is used in contract investigations by commercial service suppliers (e.g. MDS Pharma Services). In this binding assay, serial dilutions of the test compounds in DMSO are incubated with the membrane preparations and the tritium-labeled ligand nitrendipine (0.1 nM) in a 50 mM TrisHCl buffer, pH 7.7, at 25° C. typically for 90 minutes, and the specific binding of the test compounds is determined by quantifying the specifically displaced, radiolabeled ligand. $IC_{50}$ values are determined by a nonlinear regression analysis.

The $IC_{50}$ value determined in this L-type calcium channel binding assay for a conventional calcium antagonist of the dihydropyridine type such as, for example, nitrendipine is 0.3 nM, whereas the $IC_{50}$ values for investigated examples of the compounds of the invention described herein are $\geq$150 nM and thus the affinity shown for the L-type calcium channel is reduced by a factor of at least 500. Compounds with such a reduced residual binding affinity for the L-type calcium channel generally no longer show pronounced hemodynamic effects mediated by the L-type calcium channel in vivo.

3. In vivo Assay for Detecting the Cardiovascular Effect: Diuresis Investigations on Conscious Rats in Metabolism Cages Wistar rats (bodyweight 250-350 g) are kept with free access to feed (Altromin) and drinking water. From about 72 hours before the start of the test, the animals receive instead of the normal feed exclusively salt-reduced feed with a sodium chloride content of 0.02% (ssniff R/M-H, 10 mm with 0.02% Na, S0602-E081, ssniff Spezialdiäten GmbH, D-59494 Soest). During the test, the animals are housed singly in metabolism cages suitable for rats of this weight class (from Tecniplast Germany GmbH, D-82383 Hohenpeißenberg) with free access to salt-reduced feed and drinking water for about 24 hours. At the start of the test, the substance to be tested is administered into the stomach by means of gavage in a volume of 0.5 ml/kg of bodyweight of a suitable solvent. Control animals receive only solvent. Controls and substance tests are carried out in parallel on the same day. Control groups and substance-dose groups each consist of 3 to 6 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The sodium/potassium ratio is calculated from the measurements as a measure of the effect of the substance. The measurement intervals are typically the period up to 8 hours after the start of the test (day interval) and the period from 8 to 24 hours after the start of the test (night interval). In a modified test design, the urine is collected and measured at intervals of two hours during the day interval. In order to obtain a sufficient amount of urine for this purpose, the animals receive a defined amount of water by gavage at the start of the test and then at intervals of two hours.

4. DOCA/Salt Model

Administration of deoxycorticosterone acetate (DOCA) in combination with a high-salt diet and unilateral kidney removal in rats induces hypertension which is characterized by relatively low renin levels. As a consequence of this endocrine hypertension (DOCA is a direct precursor of aldosterone), there is, depending on the chosen DOCA concentration, cardiac hypertrophy and further end organ damage, e.g. of the kidney, which is characterized inter alia by protein urea and glomerulosclerosis. It is thus possible to investigate test substances in this rat model for the presence of an antihypertrophic and end organ-protecting effect.

Approximately 8-week old (body weight between 250 and 300 grams) male Sprague-Dawley (SD) rats undergo left uninephrectomy. For this purpose, the rats are anesthetized with 1.5-2% isoflurane in a mixture of 66% $N_2O$ and 33% $O_2$, and the kidney is removed through a flank incision. So-called sham-operated animals from which no kidney is removed serve as later control animals.

Uninephrectomized SD rats receive 1% sodium chloride in the drinking water and a subcutaneous injection of deoxycorticosterone acetate (dissolved in sesame oil; from Sigma) injected between the shoulder blades once a week (high dose: 100 mg/kg/week s.c.; normal dose: 30 mg/kg/week s.c.).

The substances which are to be investigated for their protective effect in vivo are administered by gavage or via the feed (from Ssniff). One day before the start of the test, the animals are randomized and assigned to groups with an identical number of animals, usually n=10, Throughout the test, drinking water and feed are available ad libitum to the animals. The substances are administered via the feed or once a day by gavage for 4-8 weeks. Animals serving as placebo group are treated in the same way but receive either only the solvent or the feed without test substance.

The effect of the test substances is determined by measuring hemodynamic parameters [blood pressure, heart rate, inotropism (dp/dt), relaxation time (tau), maximum left ventricular pressure, left-ventricular end-diastolic pressure (LVEDP)], determining the weight of the heart, kidney and lung, measuring the protein excretion, and by measuring gene expression of biomarkers (e.g. ANP, atrial natriuretic peptide, and BNP, brain natriuretic peptide) by means of RT/TaqMan PCR after RNA isolation from cardiac tissue.

Statistical analysis takes place using Student's t test after previous examination of the variances for homogeneity.

C. Exemplary Embodiments of Pharmaceutical Compositions

The compounds of the invention can be converted into pharmaceutical preparations in the following ways:

Tablet:
Composition:
100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400. 20 g of oral solution correspond to a single dose of 100 mg of the compound according to the invention.

Production:
The compound of the invention is suspended in the mixture of polyethylene glycol and polysorbate with stirring. The stirring process is continued until the compound according to the invention has completely dissolved.

i.v. Solution:
The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of the formula (I)

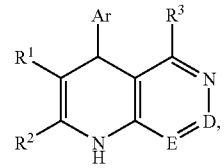

in which
D is C—$R^4$ in which
$R^4$ is hydrogen, ($C_1$-$C_6$)-alkyl, trifluoromethyl, ($C_1$-$C_6$)-alkoxy, trifluoromethoxy, ($C_1$-$C_6$)-alkylthio, amino, mono-($C_1$-$C_6$)-alkylamino or di-($C_1$-$C_6$)-alkylamino,
E is N,
Ar is a group of the formula

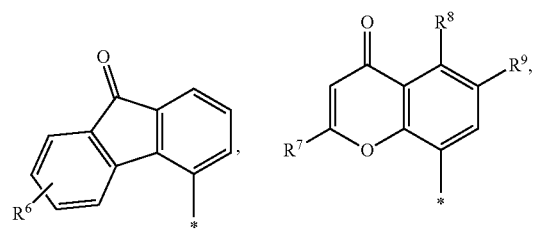

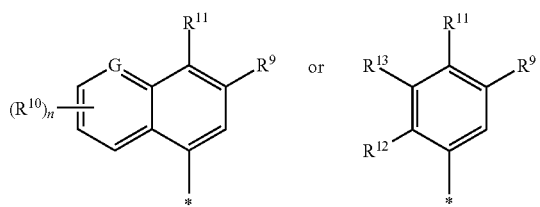

in which

* is the linkage point, $R^6$ is hydrogen or halogen, $R^7$ is methyl or ethyl, $R^8$ is hydrogen, fluorine, chlorine, cyano, nitro, trifluoromethyl or $(C_1-C_4)$-alkyl, $R^9$ is hydrogen or fluorine, $R^{10}$ is halogen, $(C_1-C_4)$-alkyl, trifluoromethyl, $(C_1-C_4)$-alkoxy or trifluoromethoxy, $R^{11}$ is cyano, $R^{12}$ is hydrogen, halogen, $(C_1-C_4)$-alkyl, $(C_1-C_4)$-alkoxy, $(C_1-C_4)$-alkylthio or di-$(C_1-C_4)$-alkylamino, it being possible for the alkyl group in said $(C_1-C_4)$-alkyl, $(C_1-C_4)$-alkoxy and $(C_1-C_4)$-alkylthio radicals in each case to be substituted up to three times by fluorine, or phenyl, which may be substituted by halogen, $(C_1-C_4)$-alkyl or trifluoromethyl, $R^{13}$ is hydrogen, halogen or $(C_1-C_4)$-alkyl, G is CH, C—$R^{10}$ or N, and n is the number 0, 1 or 2, it being possible in the case where the substituent $R^{10}$ occurs more than once for its meanings to be identical or different, $R^1$ is cyano, nitro or a group of the formula —C(=O)—$R^{14}$ or —C(=O)—O—$R^{15}$ in which $R^{14}$ is $(C_1-C_6)$-alkyl which may be substituted by $(C_3-C_7)$-cycloalkyl or once to three times by fluorine, or phenyl which may be substituted by halogen, cyano, $(C_1-C_4)$-alkyl, trifluoromethyl, $(C_1-C_4)$-alkoxy or trifluoromethoxy, or $(C_3-C_7)$-cycloalkyl, and $R^{15}$ is $(C_1-C_6)$-alkyl which may be substituted by $(C_3-C_7)$-cycloalkyl or once to three times by fluorine, or $(C_3-C_7)$-cycloalkyl, $R^2$ is $(C_1-C_4)$-alkyl, trifluoromethyl, cyclopropyl, cyclobutyl, $(C_1-C_4)$-alkoxy or $(C_1-C_4)$-alkylthio, and $R^3$ is $(C_1-C_6)$-alkyl, $(C_1-C_6)$-alkoxy, trifluoromethoxy, $(C_1-C_6)$-alkylthio, or a group of the formula —O—$SO_2$—$R^{16}$, where said $(C_1-C_6)$-alkyl, $(C_1-C_6)$-alkoxy and $(C_1-C_6)$-alkylthio radicals may in each case be substituted by $(C_3-C_7)$-cycloalkyl, and $R^{16}$ is $(C_1-C_6)$-alkyl, trifluoromethyl, $(C_3-C_7)$-cycloalkyl, phenyl or 5- or 6-membered heteroaryl having up to two heteroatoms from the series N, O and/or S, it being possible for phenyl and heteroaryl in turn each to be substituted once or twice, identically or differently, by halogen, cyano, nitro, $(C_1-C_4)$-alkyl, trifluoromethyl, $(C_1-C_4)$-alkoxy and/or trifluoromethoxy, and the salts, thereof.

2. The compound of claim 1, in which

D is C—$R^4$ in which $R^4$ is hydrogen, $(C_1-C_4)$-alkyl, $(C_1-C_4)$-alkoxy, $(C_1-C_4)$-alkylthio, amino, mono-$(C_1-C_4)$-alkylamino or di-$(C_1-C_4)$-alkylamino, E is N, Ar is a group of the formula

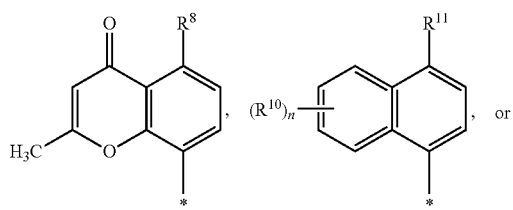

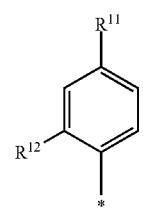

in which

* is the linkage point, $R^8$ is hydrogen, fluorine, chlorine or cyano, $R^{10}$ is fluorine, chlorine, methyl or ethyl, $R^{11}$ is cyano, $R^{12}$ is chlorine, bromine, $(C_1-C_4)$-alkyl, trifluoromethyl, $(C_1-C_4)$-alkoxy, trifluoromethoxy, $(C_1-C_4)$-alkylthio or trifluoromethylthio, and n is the number 0 or 1, $R^1$ is cyano, acetyl, trifluoroacetyl or a group of the formula —C(=O)—O—$R^{15}$ in which $R^{15}$ is $(C_1-C_4)$-alkyl which may be substituted by $(C_3-C_5)$-cycloalkyl or once to three times by fluorine, or $(C_3-C_5)$-cycloalkyl, $R^2$ is methyl or trifluoromethyl, and $R^3$ is $(C_1-C_4)$-alkoxy, trifluoromethoxy or a group of the formula —O—$SO_2$—$R^{16}$ in which $R^{16}$ is $(C_1-C_4)$-alkyl, trifluoromethyl, $(C_3-C_6)$-cycloalkyl, phenyl or thienyl, where phenyl and thienyl in turn may each be substituted once or twice, identically or differently by fluorine, chlorine, cyano, methyl, trifluoromethyl, methoxy and/or trifluoromethoxy, and the salts thereof.

3. The compound of claim 1, in which

D is C—R⁴ in which
   R⁴ is hydrogen, amino, methoxy or methylthio,

E is N,

Ar is a group of the formula

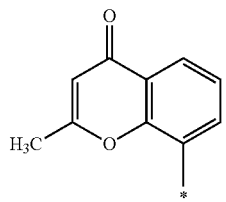 or 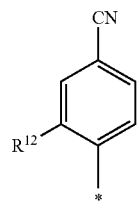

in which
   \* is the linkage point and
   R₁₂ is ethyl, methoxy or trifluoromethoxy, R¹ is cyano, acetyl, methoxycarbonyl or ethoxycarbonyl, R² is methyl or trifluoromethyl, and R³ is (C₁-C₃)-alkoxy or a group of the formula —O—SO₂—R¹⁶ in which
   R¹⁶ is (C₁-C₃)-alkyl, and the salts thereof.

4. A process for preparing compounds of the formula (I-B)

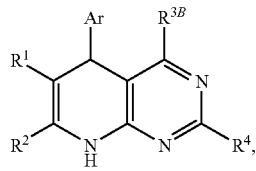 (I-B)

in which Ar, R¹, R² and R⁴ have the meanings indicated in claim 1,
and
R³ᴮ is (C₁-C₆)-alkoxy or (C₁-C₆)-alkylthio, each of which may be substituted by (C₃-C₇)-cycloalkyl, or is trifluoromethoxy, or a group of the formula —O—SO₂—R¹⁶ in which R¹⁶ has the meaning indicated in claim 1,
comprising:

condensing a compound of the formula (II)

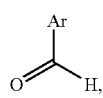 (II)

in which Ar has the meaning indicated in claim 1, with a compound of the formula (XI)

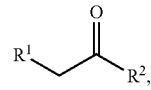 (XI)

in which R¹ and R² have the meanings indicated in claim 1, to give a compound of the formula (XII)

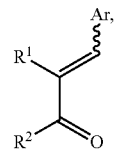 (XII)

in which Ar, R¹ and R² each have the meanings indicated above, and either

[B-1] reacting the compound of formula XII in an inert solvent with a compound of the formula (XIII)

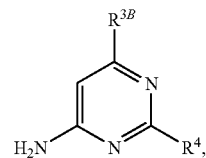 (XIII)

in which R³ᴮ and R⁴ have the meanings indicated in claim 1, or

[B-2] reacting the compound of formula (XII) in an inert solvent with a compound of the formula (XIV)

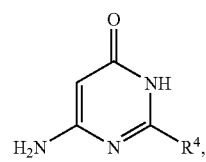 (XIV)

in which R⁴ has the meaning indicated in claim 1, to give a compound of the formula (XV)

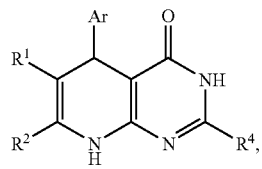 (XV)

in which Ar, R¹, R² and R⁴ each have the meanings indicated above, and either:
   alkylating the compound of formula (XV) in an inert solvent, optionally, in the presence of a base, with a compound of the formula (VIII) or a trialkyloxonium salt of the formula (IX)

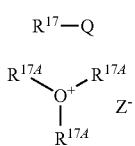 (VIII)

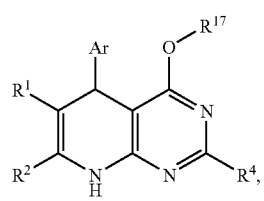 (IX)

in which
R$^{17}$ is (C$_1$-C$_6$)-alkyl which may be substituted by (C$_3$-C$_7$)-cycloalkyl, or is trifluoromethyl,
R$^{17A}$ is methyl or ethyl,
Q is a leaving group, and
Z$^{13}$ is a non-nucleophilic anion,
to give compounds of the formula (I-B 1)

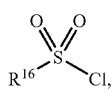 (I-B1)

in which Ar, R$^1$, R$^2$, R$^4$ and R$^{17}$ each have the meanings indicated above, or reacting the compound of formula (XV) in an inert solvent in the presence of a base with a compound of the formula (X)

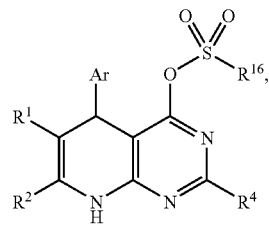 (X)

in which R$^{16}$ has the meaning indicated in claim 1, to give a compound of the formula (I-B2)

(I-B2)

in which Ar, R$^1$, R$^2$, R$^4$ and R$^{16}$ each have the meanings indicated above, wherein a racemate or diastereomeric mixture of compounds of formula (I-B), (I-B 1) or (I-B2) is optionally produced and separated by methods known to the skilled worker into their enantiomers and/or diastereomers, and/or wherein the compound of formula (I-B), (I-B 1) or (I-B2) is optionally reacted with the appropriate (i) solvent and/or (ii) base or acid to produce the solvates, salts and/or solvates of the salts thereof.

5. A pharmaceutical composition comprising a compound of the formula (I) as defined in claim 1 in combination with an inert, non-toxic, pharmaceutically suitable excipient.

6. The pharmaceutical composition of claim 5, further comprising at least one active ingredient selected from the group consisting of an ACE inhibitor, a renin inhibitor, an angiotensin II receptor antagonist, a beta-blocker, acetylsalicylic acid, a diuretic, a potassium supplement, a calcium antagonist, a statin, a digitalis (digoxin) derivative, a calcium sensitizer, a nitrate, and an antithrombotic.

* * * * *